(12) United States Patent
Moehlis et al.

(10) Patent No.: US 9,352,155 B2
(45) Date of Patent: May 31, 2016

(54) CHAOTIC DESYNCHRONIZATION OF NEURAL POPULATIONS WITH NON-PULSATILE INPUTS

(71) Applicants: The Regents of the University of California, Oakland, CA (US); University of Minnesota, Minneapolis, MN (US)

(72) Inventors: Jeffrey Michael Moehlis, Goleta, CA (US); Daniel David Wilson, Goleta, CA (US); Theoden Ivan Netoff, St. Louis Park, MN (US)

(73) Assignees: The Regents of the University of California, Oakland, CA (US); Regents of the University of Minnesota, Mineeapolis, MN (US)

( * ) Notice: Subject to any disclaimer, the term of this patent is extended or adjusted under 35 U.S.C. 154(b) by 0 days.

(21) Appl. No.: 14/420,279

(22) PCT Filed: Sep. 27, 2013

(86) PCT No.: PCT/US2013/062345
§ 371 (c)(1),
(2) Date: Feb. 6, 2015

(87) PCT Pub. No.: WO2014/052854
PCT Pub. Date: Apr. 3, 2014

(65) Prior Publication Data
US 2015/0202440 A1    Jul. 23, 2015

Related U.S. Application Data

(60) Provisional application No. 61/707,683, filed on Sep. 28, 2012.

(51) Int. Cl.
*A61N 1/00* (2006.01)
*A61N 1/36* (2006.01)
*A61N 1/378* (2006.01)

(52) U.S. Cl.
CPC ........ *A61N 1/36067* (2013.01); *A61N 1/36132* (2013.01); *A61N 1/36135* (2013.01); *A61N 1/36146* (2013.01); *A61N 1/378* (2013.01)

(58) Field of Classification Search
CPC .......... A61N 1/36067; A61N 1/36132; A61N 1/36135; A61N 1/36146; A61N 1/378; A61N 1/0526; A61N 1/0529; A61N 1/0531; A61N 1/0534; A61N 1/0536
See application file for complete search history.

(56) References Cited

U.S. PATENT DOCUMENTS 8,099,170 B2 *    1/2012    Jensen et al. .................... 607/62

* cited by examiner

*Primary Examiner* — George Manuel
(74) *Attorney, Agent, or Firm* — Lumen Patent Firm

(57) ABSTRACT

A method is provided for finding an energy-optimal stimulus which gives a positive Lyapunov exponent, and hence desynchronization, for a neural population. The method is illustrated for three different neural models. Not only does it achieve desynchronization for each model, but it also does so using less energy than recently proposed methods, suggesting a powerful alternative to pulsatile stimuli for deep brain stimulation. Furthermore, we calculate error bounds on the optimal stimulus which will guarantee a minimum Lyapunov exponent. Also, a related control strategy is developed for desynchronizing neurons based on the population's phase distribution.

5 Claims, 25 Drawing Sheets

Figs. 2A-C

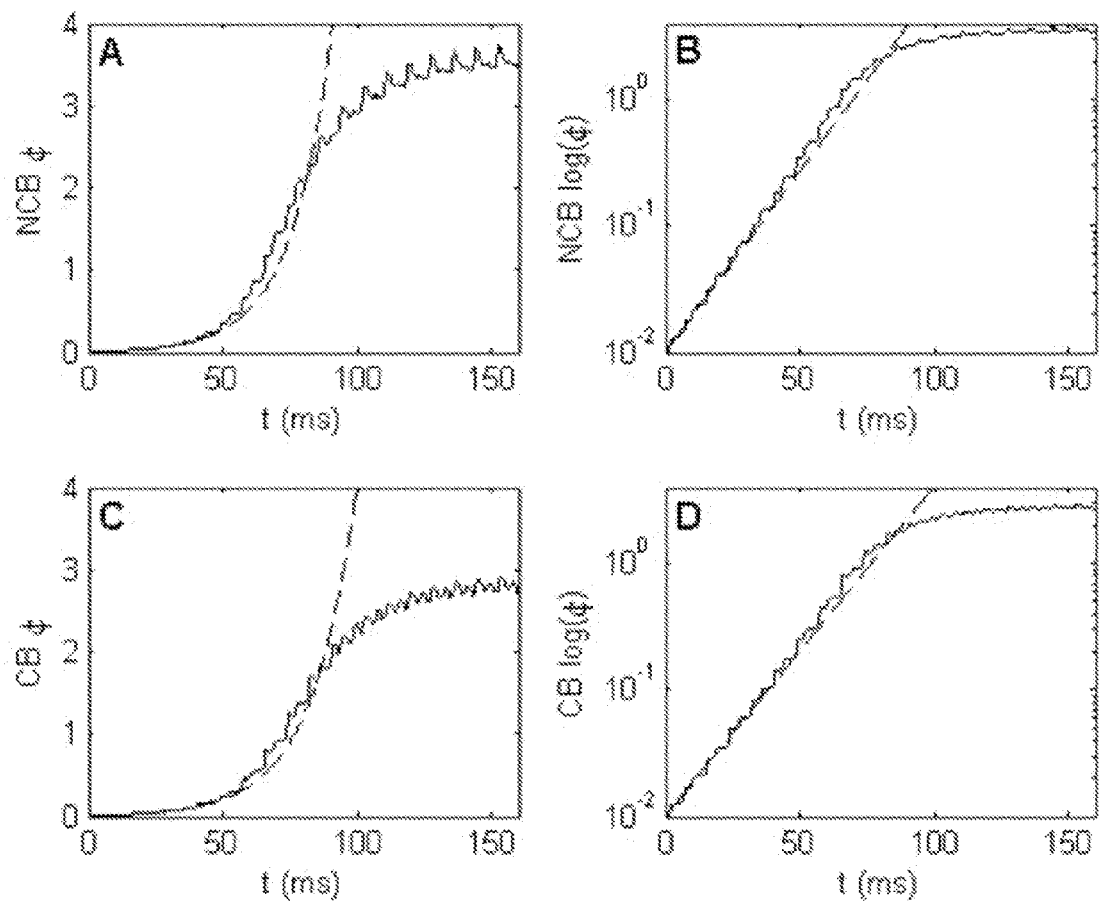
Figs. 4A-D

A
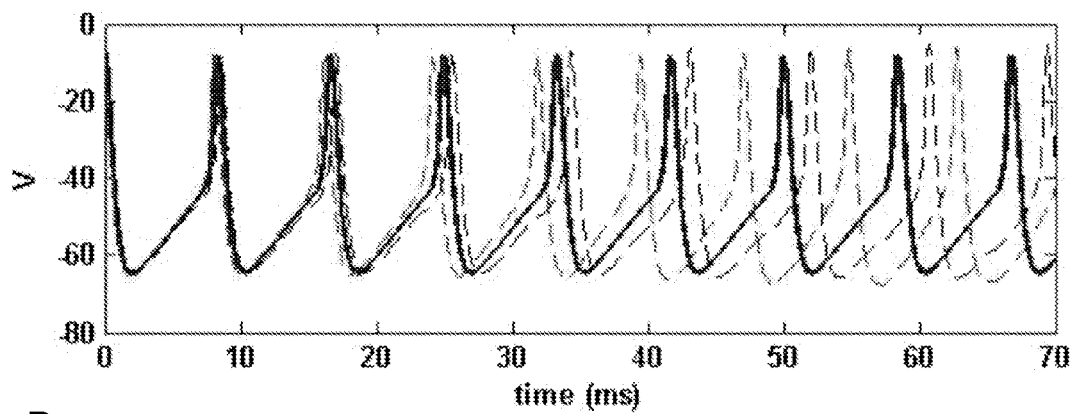
B
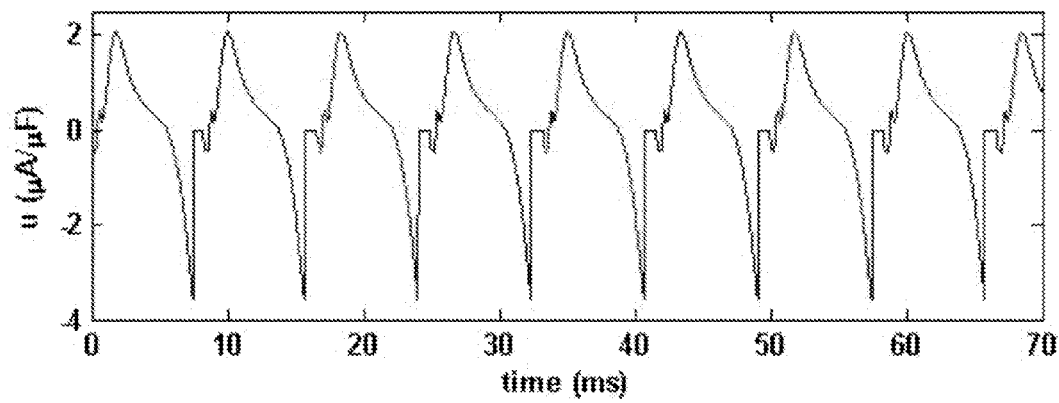
Figs. 5A-B

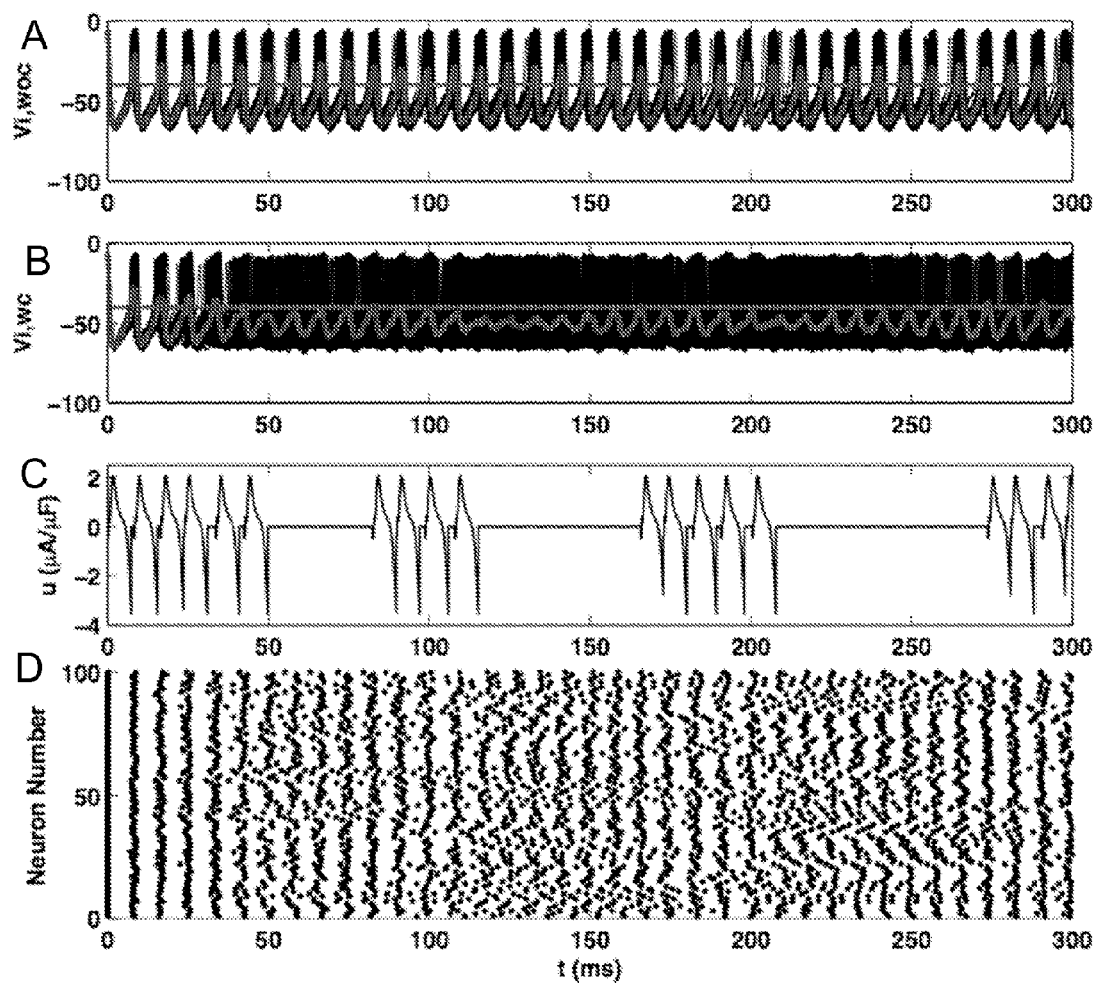
Figs. 6A-D

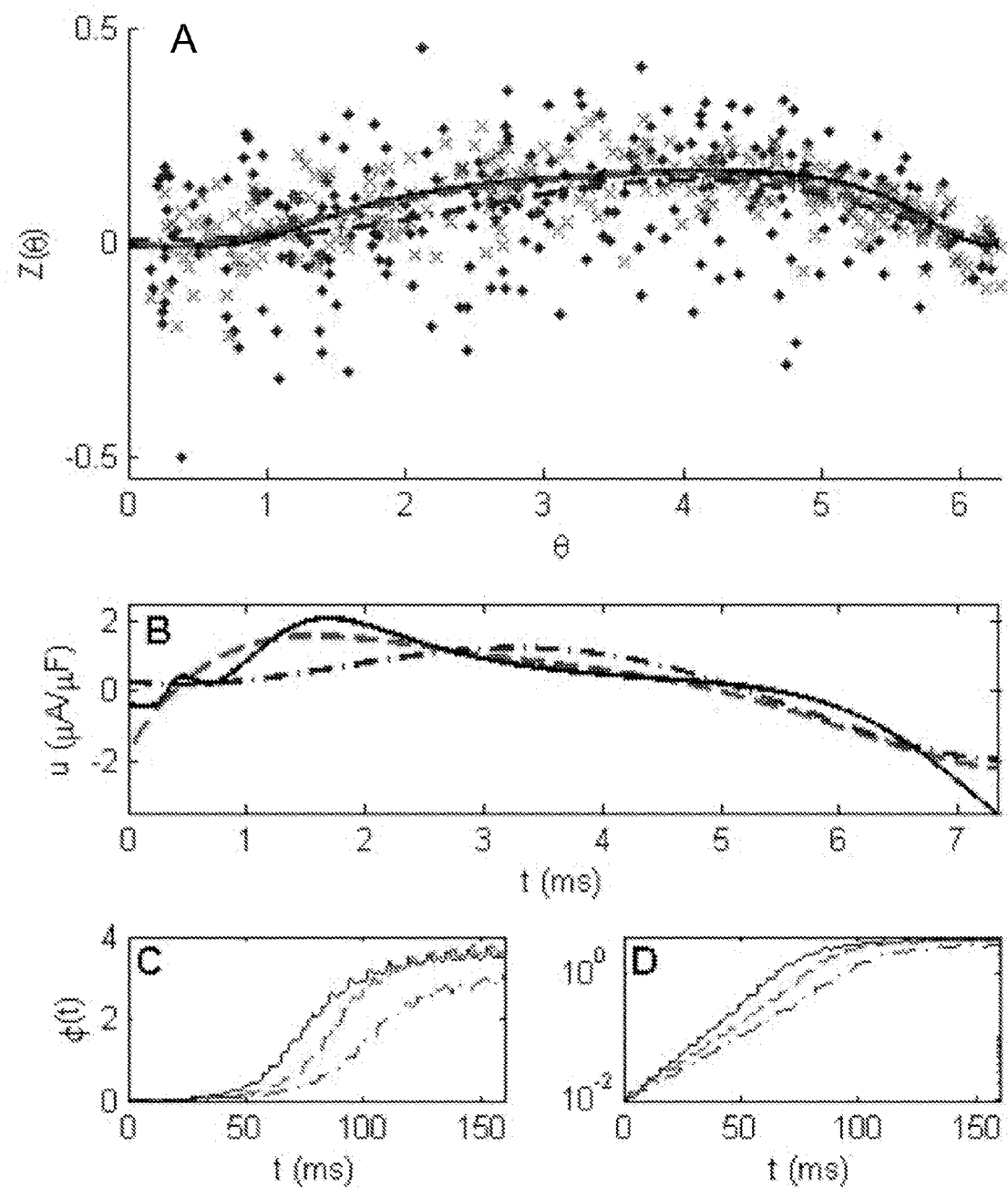
Figs. 7A-D

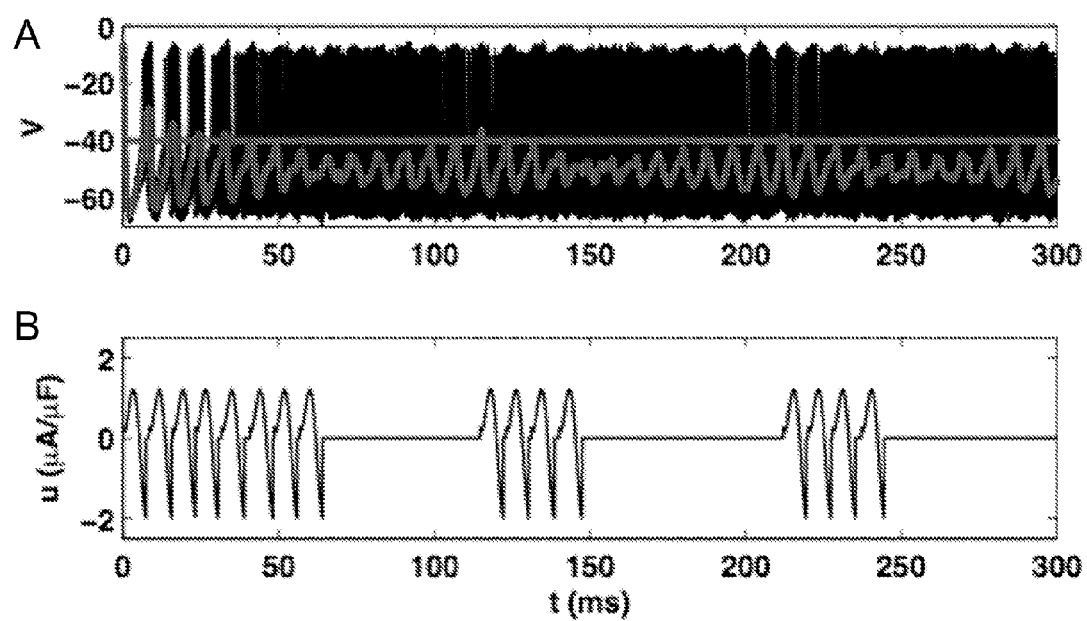
Figs. 8A-B

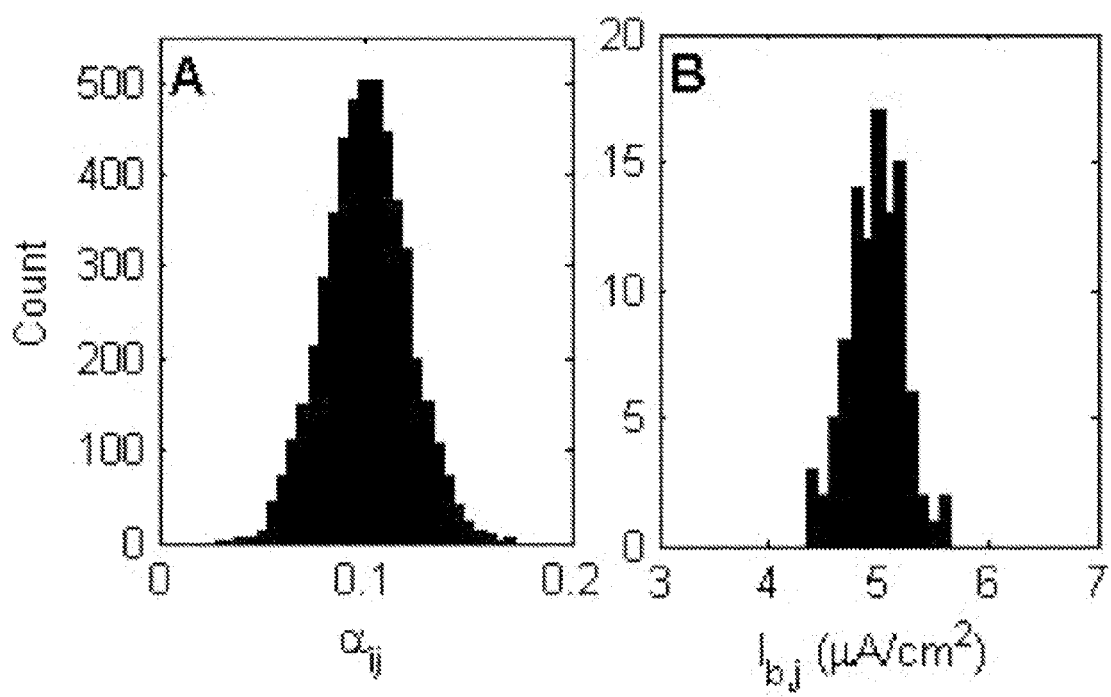
Figs. 9A-B

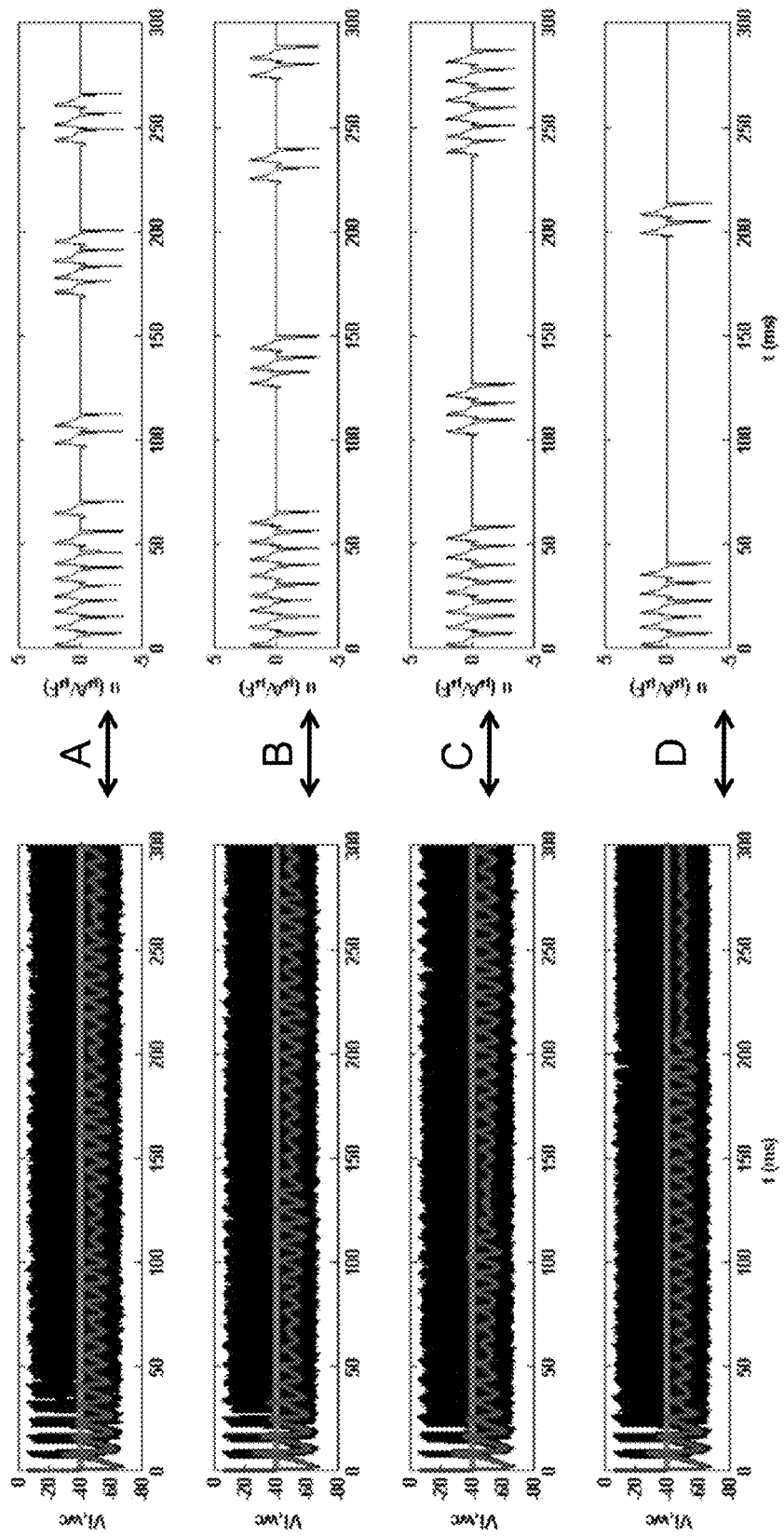
Figs. 10A-D

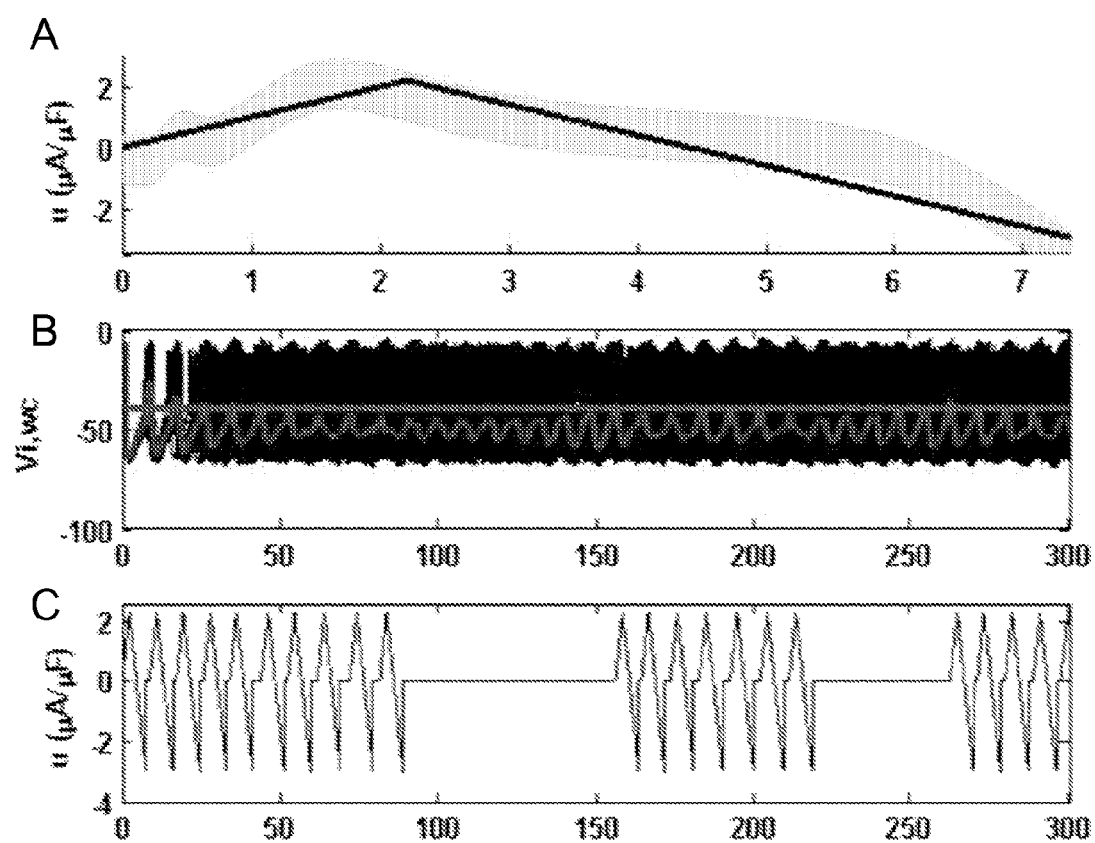
Figs. 11A-C

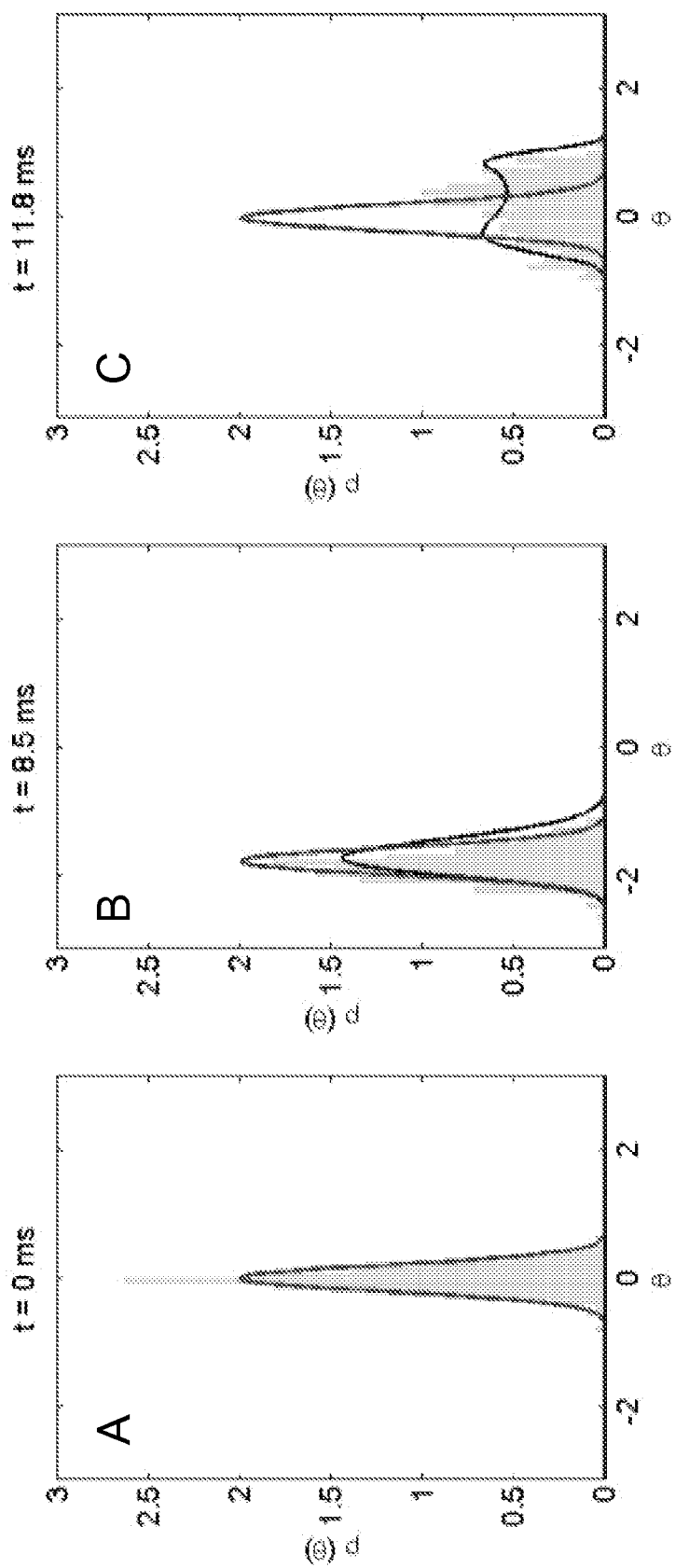
Figs. 22A-C

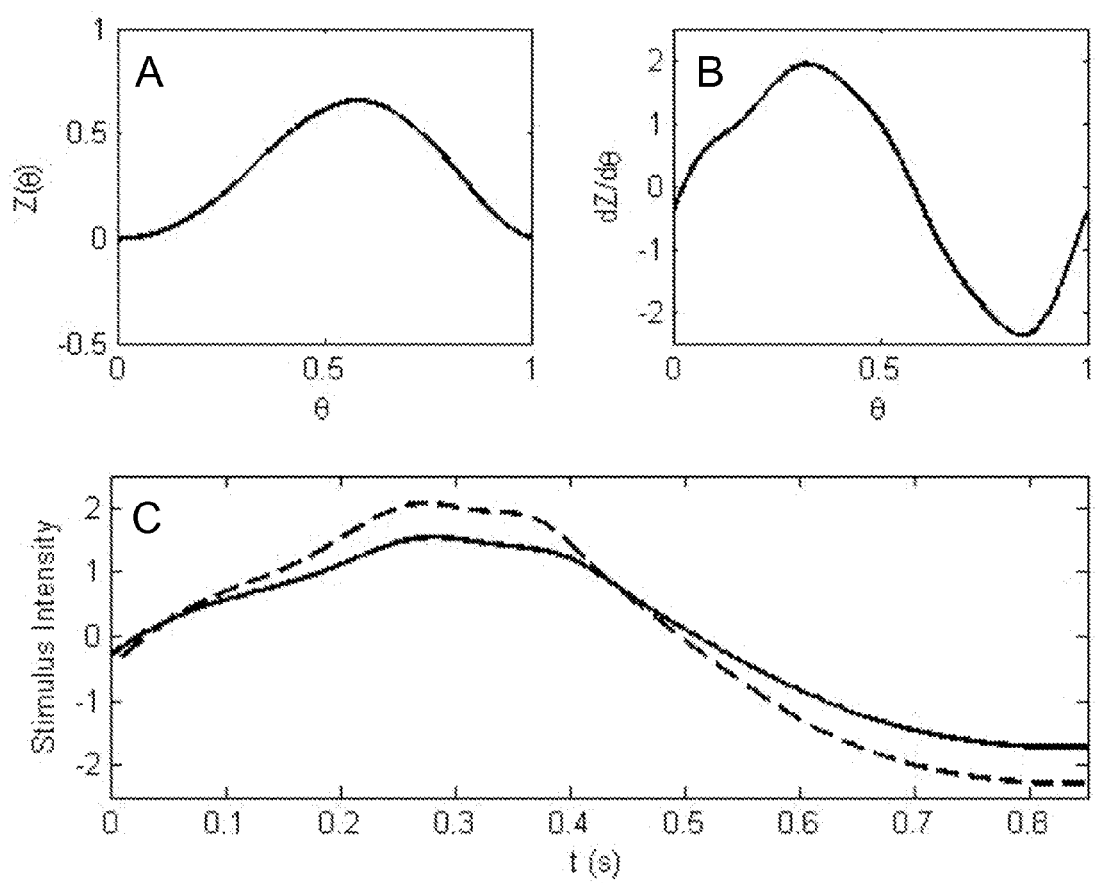
Figs. 23A-C

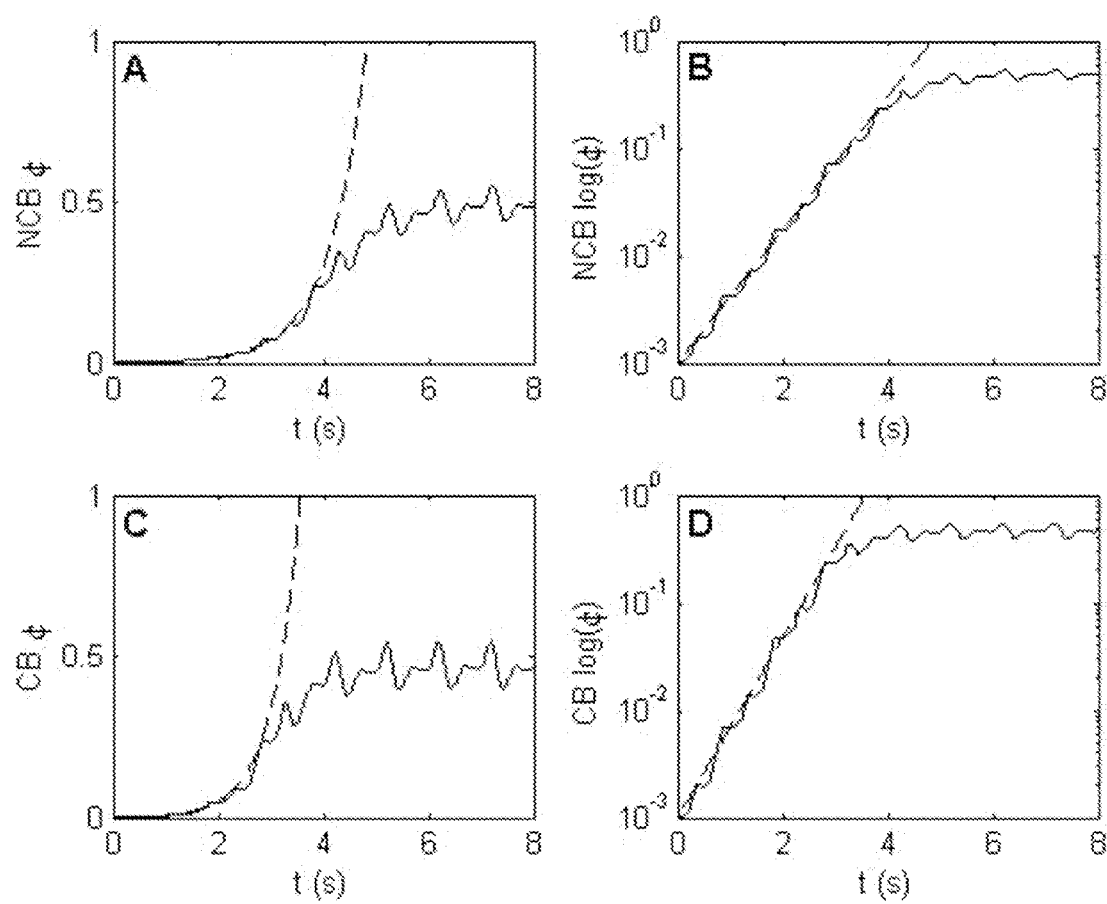
Figs. 24A-D

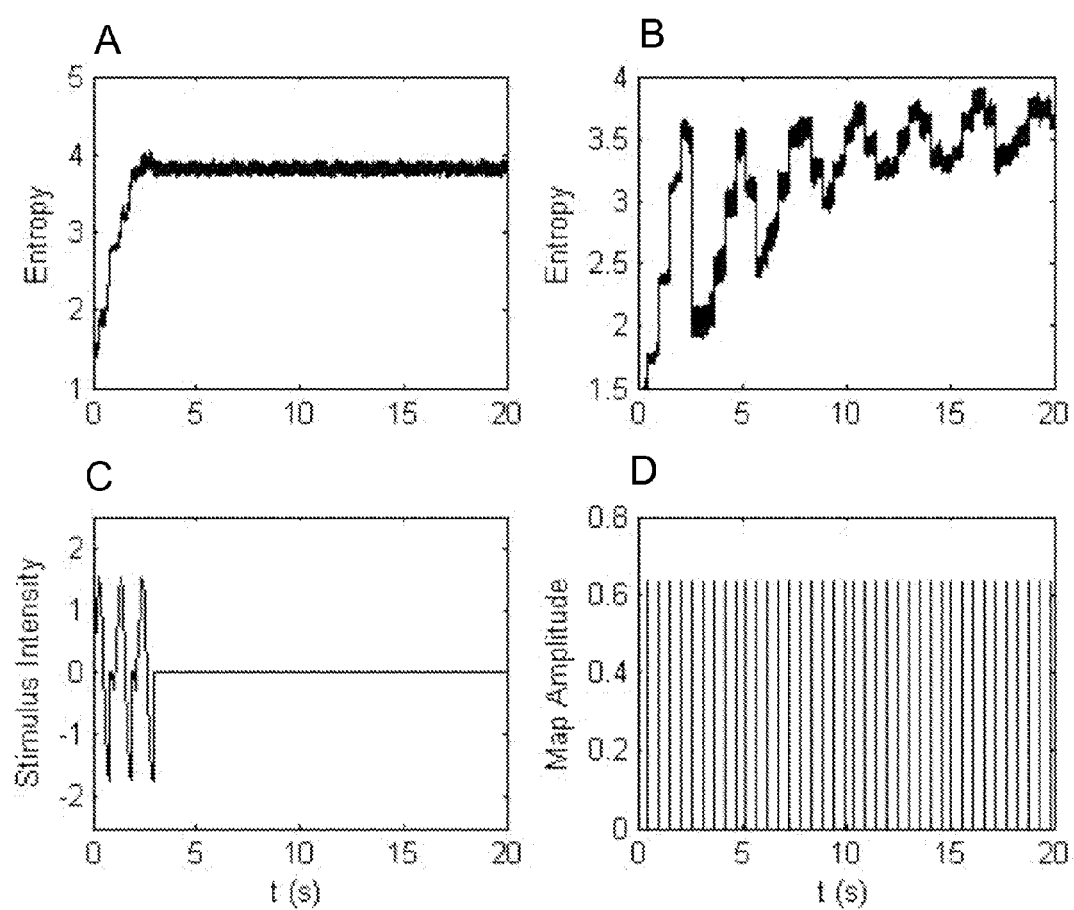
Figs. 25A-D ns with Non-Pulsatile Inputs

CHAOTIC DESYNCHRONIZATION OF NEURAL POPULATIONS WITH NON-PULSATILE INPUTS

CROSS-REFERENCE TO RELATED APPLICATIONS

This application is a 371 of PCT application PCT/US2013/062345 filed on Sep. 27, 2013. PCT application PCT/US2013/062345 filed on Sep. 27, 2013 claims the benefit of US Provisional application 61/707683 filed on Sep. 28, 2012.

STATEMENT OF GOVERNMENT SPONSORED SUPPORT

This invention was made with Government support under contract no. 1000678 awarded by the National Science Foundation (NSF). The Government has certain rights in the invention.

FIELD OF THE INVENTION

This invention relates to deep brain stimulation. In particular, the invention relates to deep brain stimulation using chaotic desynchronization of neural populations.

BACKGROUND OF THE INVENTION

Pathological synchronization among spiking neurons in the basal ganglia-cortical loop within the brain is thought to be one factor contributing to the tremors exhibited by patients with Parkinson's disease. Deep Brain Stimulation (DBS), a well-established technique for mitigating these tremors, has been hypothesized to desynchronize these neurons through the injection of a high-frequency, pulsatile input into an appropriate region of the brain. Typically, DBS is implemented with a permanent, high frequency, pulsatile signal which is administered in an open-loop fashion. This has motivated researchers to search for alternative stimuli that consume less energy to prolong battery life and to mitigate side effects of DBS such as aggregate tissue damage. Control methods that employ feedback control are of particular interest because they can be used only when needed.

For example, double-pulse stimulation was shown to desynchronize a population of noisy phase oscillators and prevent resynchronization. Nonlinear, time-delayed feedback is used to experimentally desynchronize a system of electro-chemical oscillators. A minimum time desynchronizing control was used based on phase resetting for a coupled neural network was established using a Hamilton-Jacobi-Bellman approach, which was later extended to desynchronize neurons using an energy-optimal criterion. An energy-optimal, charge-balanced stimulus was used to control neural spike timing. More recently, a model was developed to control neural networks using a light sensitive protein, instead of electrical stimuli. The present invention advances the art of DBS by using chaotic desynchronization of neural populations.

SUMMARY OF THE INVENTION

The present invention advances the art by using desynchronization of neurons using stimuli which require less power allowing the pacemakers' battery to last longer, reducing the stimulis' effect on other parts of the brain, and reducing the likelihood of adaptation by the neurons. In one example, the invention pertains to a device and method in which optimal or near optimal DBS stimuli are calculated. This calculation uses the phenomenon of chaos to desynchronize a population of neurons. In particular, it uses optimal control theory to simultaneously optimize for minimum energy usage and maximum Lyapunov exponent (a measure of the rate of separation of two trajectories that are initially close together).

In one variation, these new methods of the present invention could be used to optimally synchronize a population of oscillators (neurons or otherwise) by setting the coefficient which multiplies the Lyapunov Exponent in the cost function to be negative. The stimuli in this invention are determined from the neuronal population's phase response curves. In one example, these curves can be calculated numerically for mathematical models of neurons and are experimentally measurable. Accordingly, a patients' physiological response to stimuli is used to determine the optimal stimulus for desynchronizing the neurons. In one variation, one could use other measures for characterizing the neural response such as Wiener Kernels or Volterra Series. Another variation is the use of optimal control theory to design a stimulus that reduces the value of the peak of a phase that maximally distributes the phases of the neurons in a population of neurons In another variation, other measures could be optimized such as entropy of a neural population.

In another variation, the calculation can be modified to give stimuli that are charge-balanced.

As it is believed by the inventors that the pathological synchronization is due to coupling between neurons or due to the presence of common inputs, embodiments of the invention will result in more effective therapeutic desynchronization of populations of neurons and do so with less power compared to existing techniques which for example use periodic pulsatile stimuli or other existing approaches. In addition, the approach of this invention could be used in conjunction with the constant monitoring of the patients' response to stimuli to adaptively update the stimulus to maintain efficacy.

Unlike prior methods, the method of this invention does not need the full model for the dynamics, and it only requires a single input. In addition, some prior methods use delayed-feedback stimulation to counter the effects mean field coupling on an ensemble of heterogeneous oscillators, however, the method of this invention notably differs from these methods because it is applicable to networks without mean-field coupling, and does not require simultaneous stimulation and measurement. We have compared the present method to other recently proposed methods, not only to show its desynchronizing capabilities for many types of neural models, but also its ability to do so with comparatively small control inputs. Furthermore, we have computed error bounds on the optimal stimulus that will guarantee a resulting signal that will have the required properties to desynchronize a network of neurons, and provide a control strategy for desynchronizing a population based on its phase distribution.

FIGS. 4A-D show according to an exemplary embodiment of the invention (A-B) a phase difference between two neurons over time for the NCB optimal stimulus (giving $\Lambda=0.066$) applied repeatedly to two neurons with nearly identical initial phases. (C-D) show the same plots for the CB stimulus ($\Lambda=0.060$). In both cases the neurons desynchronize at a rate determined by $\Lambda$, calculated from equation (4), until $\phi$ is approximately 2 at which point the solution begins to asymptote to $\phi$ is approximately $\pi$, i.e. the anti-phase state. Dashed lines show exponential functions based on the Lyapunov exponents.

FIGS. 5A-B show according to an exemplary embodiment of the invention time histories of three neurons with initial conditions $\theta=-0.1, 0,$ and $+0.1$ on the periodic orbit. A new stimulus is applied each time the reference neuron with initial phase $\theta=0$ fires.

FIGS. 6A-D show according to an exemplary embodiment of the invention results for a population of N=100 noisy, coupled neurons. The first panel (A) shows the network in the absence of control. The second (B) and third (C) panels show results for the same network with the event-based control applied. The traces (D) give the mean voltages for the system and the horizontal dotted line shows the control activation threshold. Substantial desynchronization can be seen from the raster plot.

Figure 1:
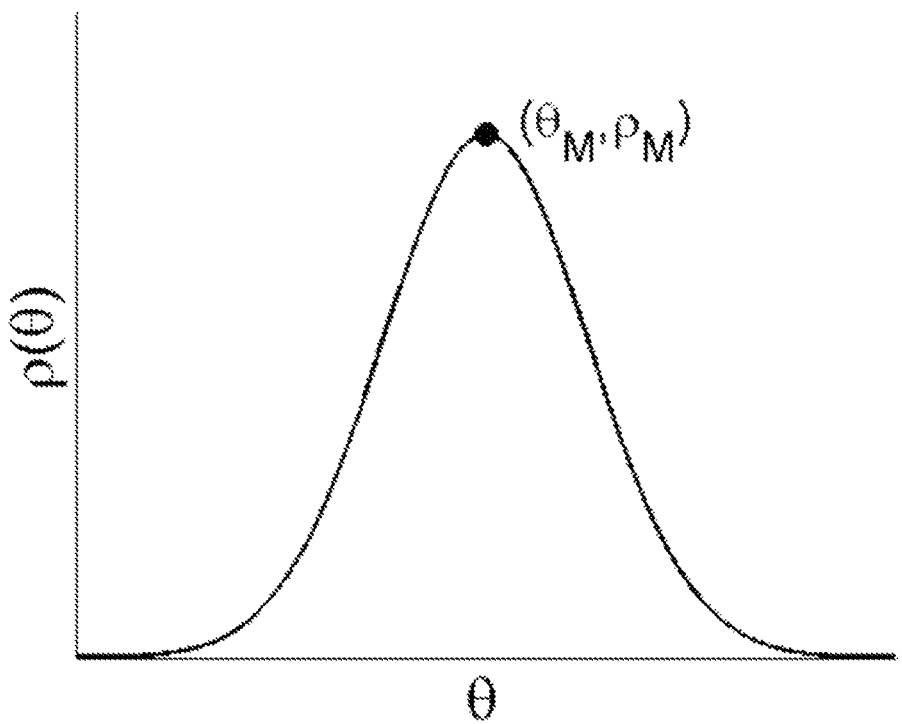
FIG. 1 shows the maximum value, $\rho_M$ for a large distribution of neurons according to an exemplary embodiment of the invention.
Figure 2:
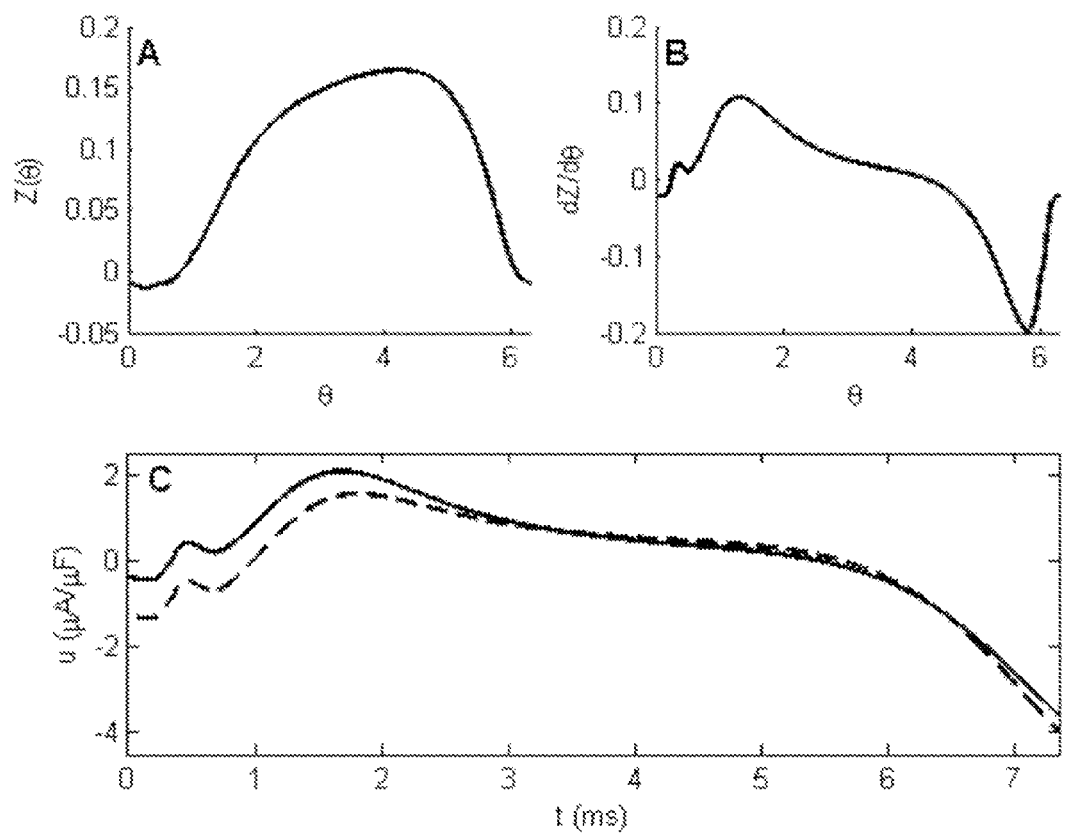
FIGS. 2A-C show according to an exemplary embodiment of the invention (A-B) numerically computed PRC and its derivative for the thalamus model. (C) The CB and NCB optimal stimuli are shown as a dashed and solid line, respectively.

FIGS. 7A-D show according to an exemplary embodiment of the invention (A) Obtaining the PRC from a noisy system with the direct method. Data points associated with noise level D=1 and 0.25 are shown as dots and x's, respectively, with 6th order polynomial fits given as a dashed and dot-dashed line, respectively. Pearson Correlation coefficients of the polynomial fits for D=1 and 0.25 are 0.3617 and 0.6638, respectively. For comparison, the numerically computed (exact) PRC is shown as a solid line. (B) NCB optimal stimuli computed with experimentally determined PRCs with D=1 and 0.25 are shown as dot-dashed and dashed lines, respectively. The true NCB optimal stimulus from FIG. 2 is shown as a solid line for reference. (C-D) Phase differences between two neurons over time for the optimal stimulus obtained from systems with noise level D=1, 0.25, and 0 applied repeatedly to two neurons with dynamics governed by the exact PRC and with close initial phase differences are shown as dot-dashed, dashed, and solid lines, respectively.

FIGS. 8A-B show according to an exemplary embodiment of the invention results for a population of N=100 noisy, coupled neurons with optimal stimulus found using the direct method for a noisy (D=1) neuron. The top (A) and bottom (B) panels show results for the network with the event-based control applied. The traces give the mean voltages for the system and the horizontal dashed line shows the control activation threshold.

FIGS. 9A-B show according to an exemplary embodiment of the invention (A) Normal distributions of the coupling strengths with $\alpha_{ij} \in N(0.1, 0.02)$. (B) Normal distributions of the baseline currents with $I_{b,j} \in N(5, 0.25)$.

FIGS. 10A-D show according to an exemplary embodiment of the invention results for a population of N=100 coupled neurons with i.i.d. noise strength D=1. The top panel (A) shows a network with homogeneous coupling strength $\alpha_{ij}=0.1$ and baseline current $I_b=5$ µA/cm2. In the second panel (B), coupling strengths drawn from a distribution as shown in panel A of FIG. 9 but baseline current is the same for all neurons, $I_b=5$ µA/cm². In the third panel (C) baseline currents are drawn from a distribution as shown in panel B of FIG. 9, but coupling is the same for all neurons, $\alpha_{ij}=0.1$. The bottom panel (D) shows a network with both heterogeneous baseline currents and coupling strengths drawn from the corresponding distributions in FIG. 9. Once the network is sufficiently desynchronized, the controller will only activate once the voltage has crossed the threshold, shown as a horizontal line.

FIGS. 11A-C show according to an exemplary embodiment of the invention results for the population of N=100 coupled neurons from FIG. 4 with the simple, piecewise linear stimulus from. The top panels (A) shows the stimulus as well as a shaded boundary that will ensure sufficient desynchronization. The traces in the middle panel (B) give the mean voltages for the system and the horizontal line gives the control activation threshold. We see in the third panel (C) that desynchronization occurs, but requires more applications of the stimulus than the optimal stimulus, which is expected due to a smaller Lyapunov exponent.

Figure 12:
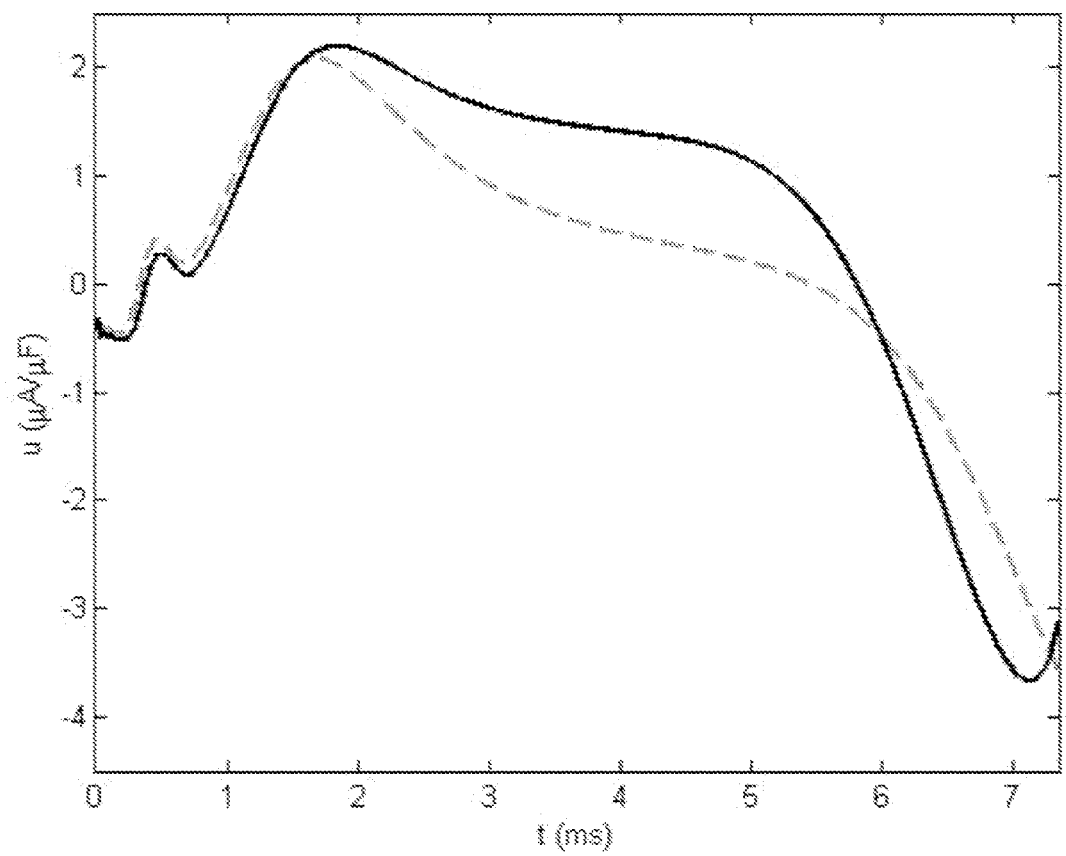

FIG. 12 shows according to an exemplary embodiment of the invention the optimal stimulus $u_D$ for decreasing the peak of the phase distribution is shown as a solid, black line. For reference, the NCB optimal stimulus for maximizing the Lyapunov exponent is shown as a grey, dashed line.

Figure 13:
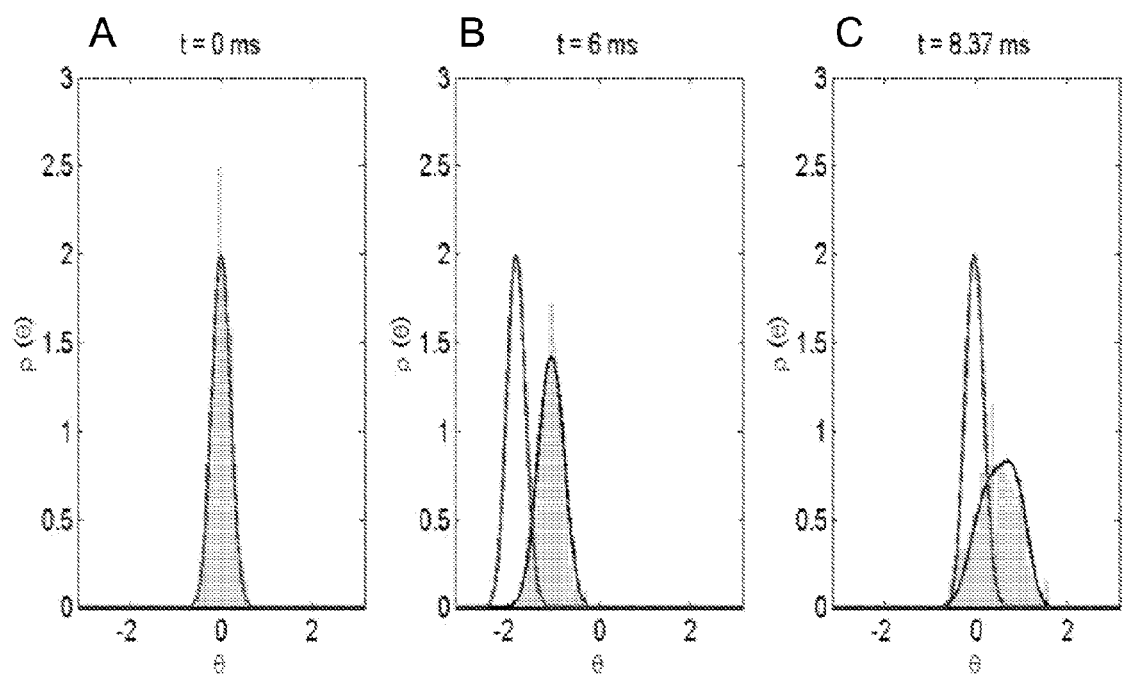
Figure 14:
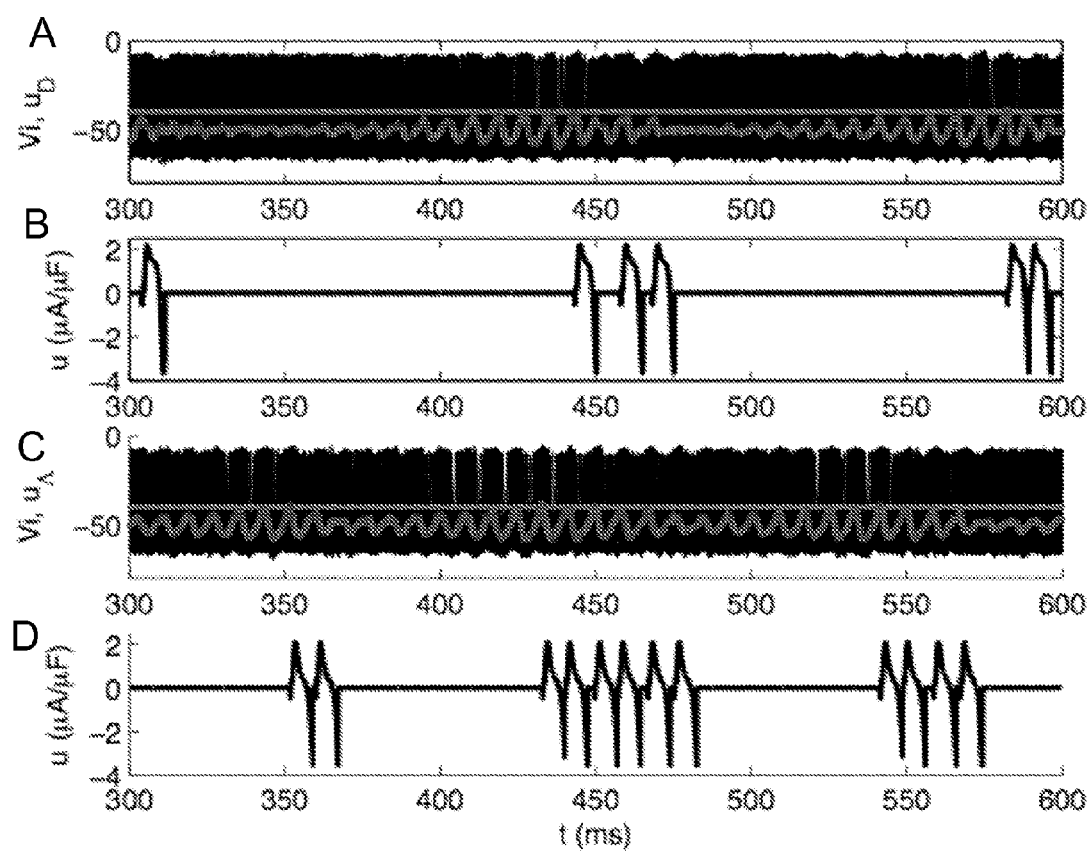

FIGS. 13 A-C show according to an exemplary embodiment of the invention three panels (A-C) with results, the mapping $\theta \in (\pi, 2\pi) \to (-\pi, 0)$ is used, e.g., $$\theta = \frac{3\pi}{2}$$

is plotted as $$\theta = -\frac{\pi}{2}.$$

Theoretical and numerical evolutions are shown in black and grey-shaded-areas, respectively. The theoretical evolution of the distribution in the absence of stimulus and is shown for reference (light grey line).

FIGS. 14A-D show according to an exemplary embodiment of the invention a comparison between $u_D$ to $u_A$. Representative excerpts from a 1000 ms simulation using $u_D$ to $u_A$ as the control are shown in the top (A-B) and bottom panels (C-D), respectively.

FIGS. 15A-C show according to an exemplary embodiment of the invention top panels where (A-B) show the numerically computed PRC and its derivative for the reduced Hodgkin-Huxley model. The bottom panel (C) shows The CB and NCB optimal stimuli as a dashed and solid line, respectively.

FIGS. 16A-D show according to an exemplary embodiment of the invention (A-B) the phase difference between two neurons over time for the NCB optimal stimulus (giving $\Lambda=0.0823$) applied repeatedly to two neurons with nearly identical initial phases. (C-D) show the same plots for the CB stimulus ($\Lambda=0.0782$). In both cases the neurons desynchronize at a rate determined by $\Lambda$, calculated from (4) until $\phi$ is approximately 1. Dashed lines show exponential functions based on the Lyapunov exponents.

Figure 17:
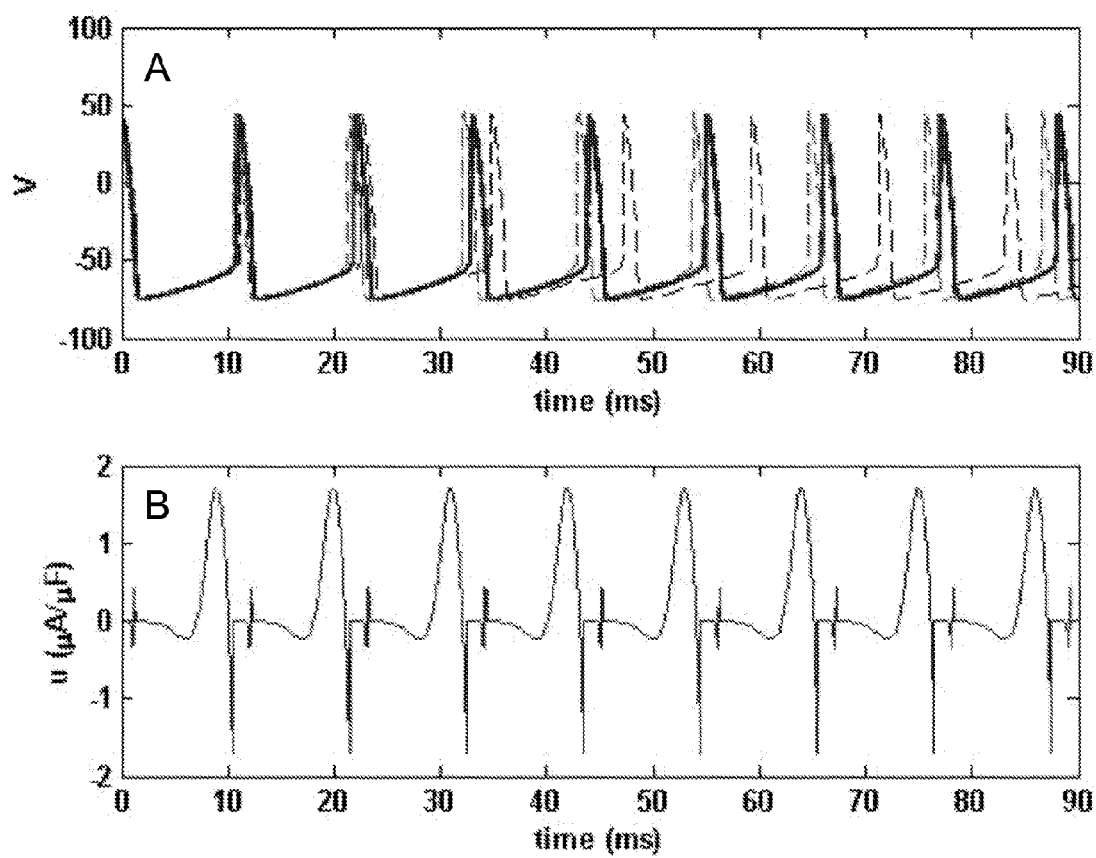

FIGS. 17A-B show according to an exemplary embodiment of the invention time histories of three neurons with initial conditions $\theta=-0.1, 0,$ and $+0.1$ on the periodic orbit. A new stimulus is applied each time the reference neuron with initial phase $\theta=0$ (shown as a black line) fires. Once the neurons are no longer close in phase, the neuron which started ahead of the reference neuron desynchronizes faster than the neuron that starts behind the reference neuron which can be explained by the shape of the PRC, as described in the main text.

Figure 18:
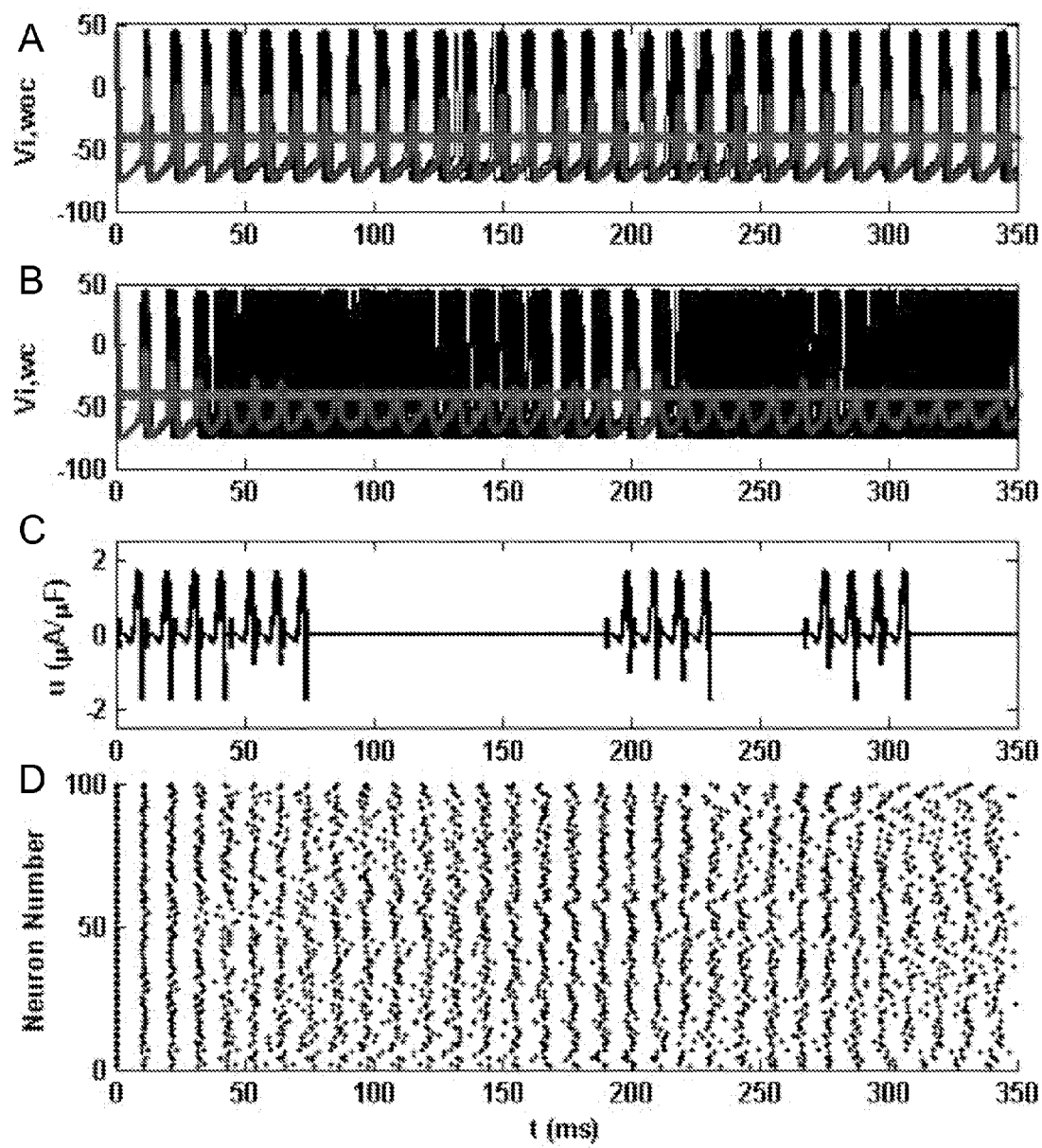

FIGS. 18 A-D show according to an exemplary embodiment of the invention results for a population of N=100 noisy, coupled neurons obeying the reduced Hodgkin-Huxley model. The first panel shows results in the absence of control. The second and third panels show results for the same network with the event-based control applied. The traces give the mean voltages for the system and the horizontal line shows the control activation threshold. Substantial desynchronization can be seen from the raster plot.

Figure 19:
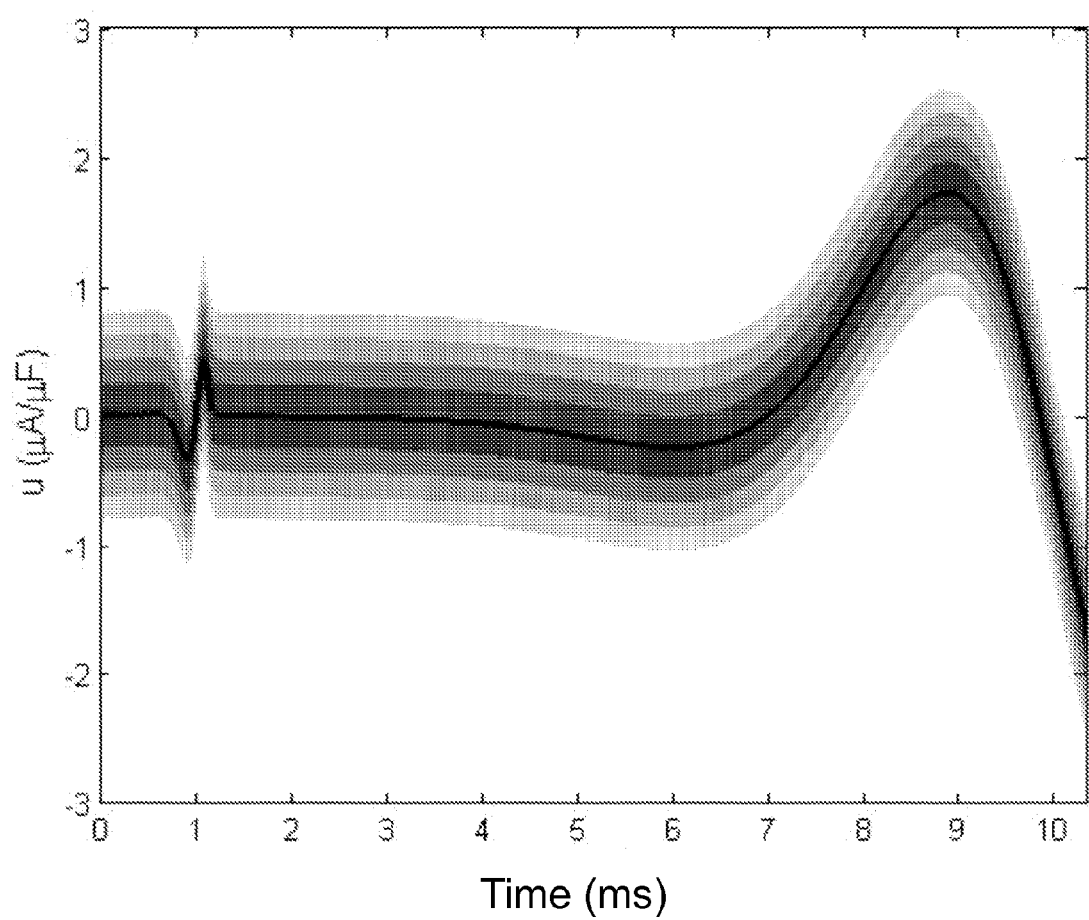
Figure 20:
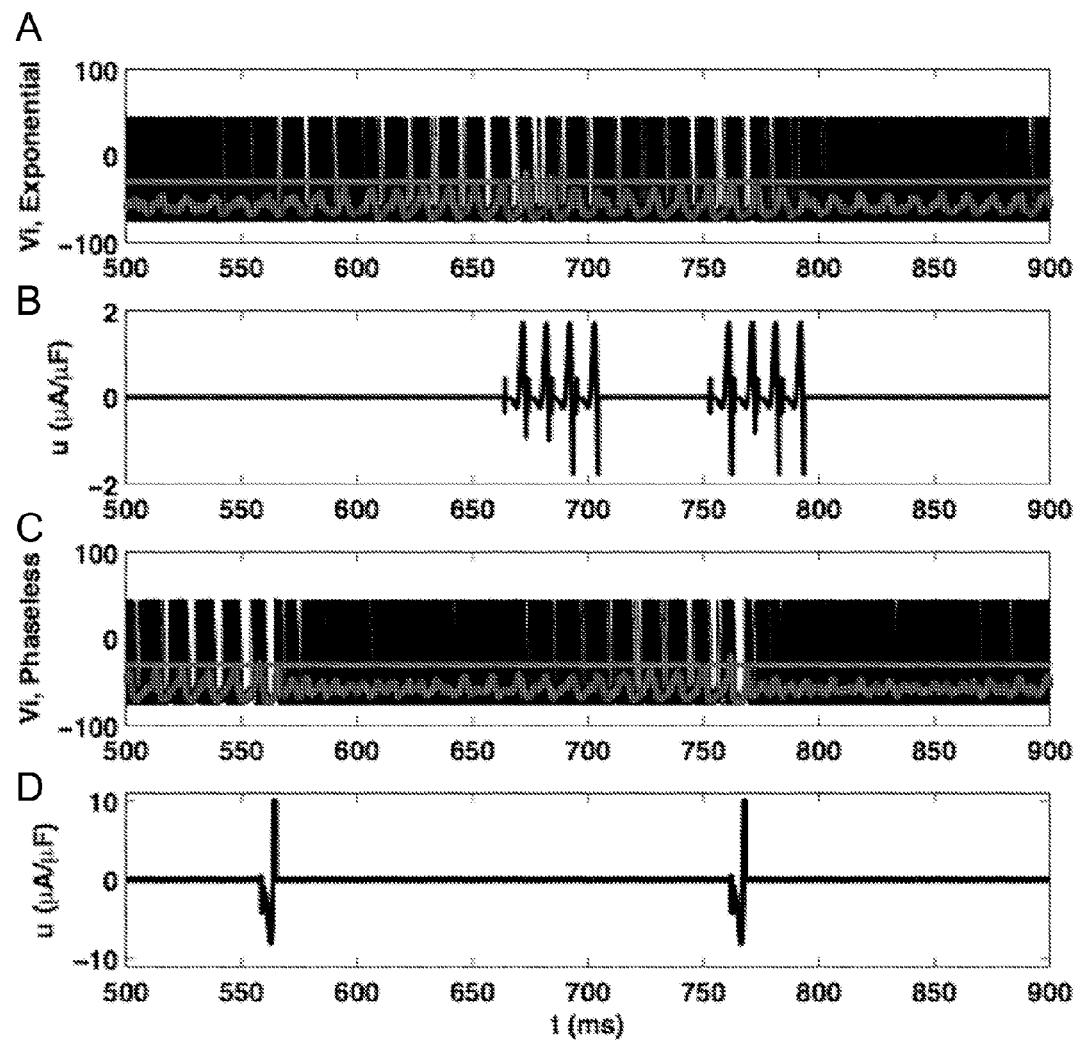

FIG. 19 shows according to an exemplary embodiment of the invention the optimal NCB stimulus, shown as a solid line, yields $\Lambda=0.0823$. In order to guarantee a stimulus with $\Lambda \geq 0.06, 0.04, 0.02,$ and $0$, we require $\|Ie(t)11\| \leq 0.242, 0.440, 0.615,$ and $0.797$, respectively, for all t. Darker shaded regions on the plot correspond to regions with larger guaranteed Lyapunov exponents.

FIGS. 20A-D show according to an exemplary embodiment of the invention a comparison of the NCB optimal (exponential) control to the phaseless control. Representative excerpts from a 1500 ms test of the exponential and phaseless control are shown in the top and bottom panels, respectively. The exponential control fires more often than the phaseless control, but uses less energy because the magnitude of the stimulus is much smaller.

Figure 21:
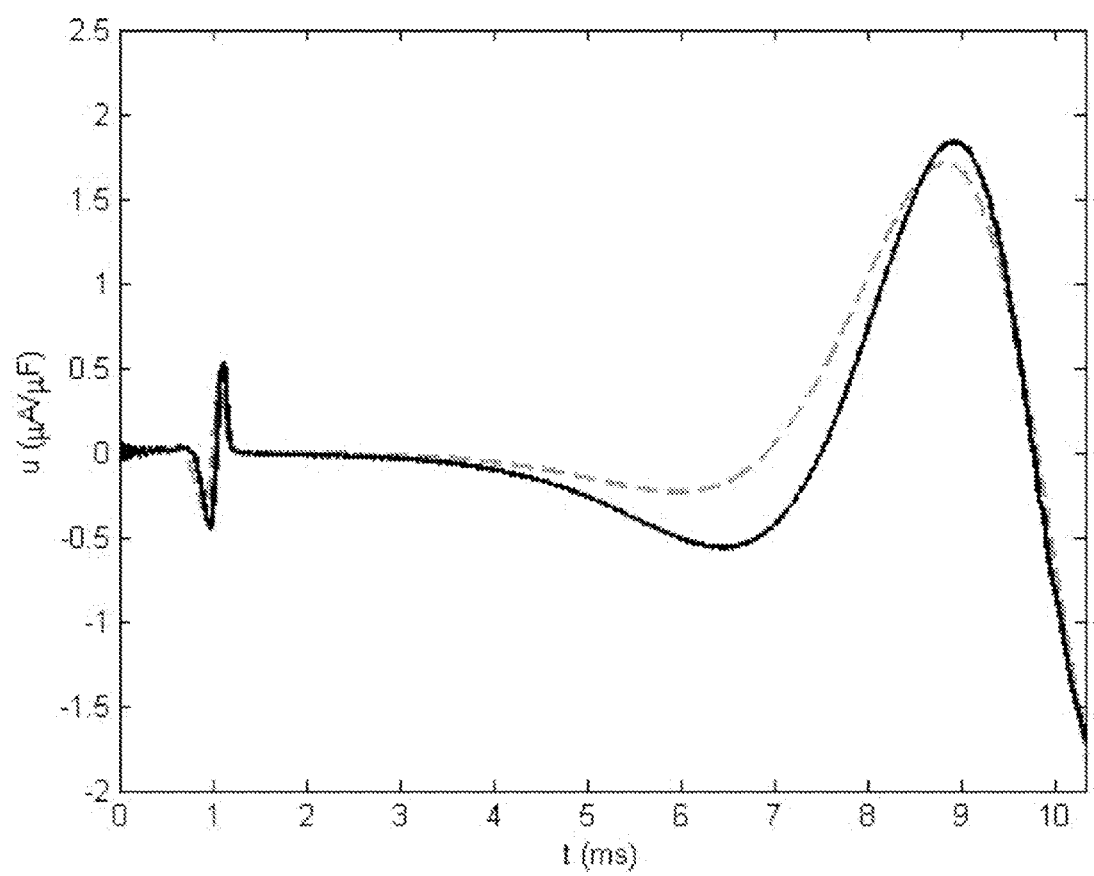

FIG. 21 shows according to an exemplary embodiment of the invention the optimal stimuli for decreasing the peak of a distribution is shown as a solid, black line. For reference, the NCB optimal stimulus for maximizing the Lyapunov exponent is shown as a grey, dashed line.

FIGS. 22A-C show according to an exemplary embodiment of the invention three frames with the mapping $\theta \in (\pi, 2\pi) \to (-\pi, 0)$ is used, e.g., $$\theta = \frac{3\pi}{2}$$

is plotted as $$\theta = -\frac{\pi}{2}.$$

Theoretical and numerical evolutions are shown in black and grey-shaded-area, respectively. The theoretical evolution of the distribution in the absence of stimulus and is shown for reference—grey line.

FIGS. 23A-C show according to an exemplary embodiment of the invention with top panels (A-B) the PRC and its derivative for the model used in the inventors' prior work. The bottom panel (C) shows the CB and NCB optimal stimuli as a dashed and solid line, respectively.

FIGS. 24A-D show according to an exemplary embodiment of the invention (A-B) the phase difference between two neurons over time for the NCB optimal stimulus (giving $\Lambda=1.429$) applied repeatedly to two neurons with nearly identical initial phases. (C-D) give the same plots for the CB stimulus ($\Lambda=1.937$). In both cases the neurons desynchronize at a rate determined by $\Lambda$, calculated from (4) until $\phi$ is approximately 0.25 at which point the solution begins to asymptote to $\phi \approx 0.5$, i.e., the anti-phase state. Dashed lines show exponential functions based on the Lyapunov exponents.

FIGS. 25A-D show according to an exemplary embodiment of the invention left panels (A, C) the entropy of 100 neurons and the applied stimulus for the exponentially desynchronizing control. The right panel (B, D) shows entropy of 100 neurons for the pulsatile input applied at 1.92 Hz. Note that the bottom-right panel (D) shows the map amplitude, $\delta$, and not the stimulus intensity to emphasize that the stimuli are simulated as delta functions. Each pulse uses 108 units of energy.

DETAILED DESCRIPTION

Derivation of the Lyapunov Exponent and Optimal Control

A method is provided for finding an energy-optimal DBS stimulus which exponentially desynchronizes a population of neurons. An advantage of this approach is that it only requires knowledge of a neuron's phase response curve (PRC), which is experimentally measurable by perturbing an oscillatory neuron at different phases, and determining the change in spike timing. The PRC can also be calculated numerically if all equations and parameters in the neural model are known. Through phase reduction, we can obtain a reduced model for a single neuron of the form $$\frac{d\theta}{dt} = \omega + Z(\theta)u(t), \tag{1}$$

where $\theta$ is the phase of the neuron and is $2\pi$-periodic on $[0, 2\pi)$ and, by convention, $\theta=0$ corresponds to the spiking of the neuron. Here, $\omega$ gives the neuron's baseline dynamics which are determined from its natural period T as $\omega=2\pi/T$, $Z(\theta)$ is the PRC, and $u(t)=I(t)/C$ with $I(t)$ being the control input and $C=1\ \mu F/cm^2$ is the constant neural membrane capacitance.

Lyapunov exponents are used to describe the rate at which nearby trajectories diverge, and have proven useful in other problems, for example, by serving as biomarkers for seizure prediction and control. We now derive an expression for the Lyapunov exponent for (??) by considering two identical neurons subject to a common stimulus:

$$\frac{d\theta_i}{dt} = \omega + Z(\theta_i)u(t), i = 1, 2. \tag{2}$$

Here we assume that the neurons are nearly in-phase, so that $\theta_1 \approx \theta_2$. Letting $\phi \equiv |\theta_2 - \theta_1|$, we obtain $$\frac{d\phi}{dt} = Z'(\theta)u(t)\phi + O(\phi^2). \tag{3}$$

Since we have linearized the equation, we assume that solutions are of the form $\phi \sim e^{\Lambda t}$, which yields the finite time Lyapunov exponent $$\Lambda(\tau) = \frac{\log(\phi(\tau))}{\tau} = \frac{\int_a^{a+\tau} Z'(\theta(s))u(s)\,ds}{\tau}. \tag{4}$$

We now consider a population of neurons, each described by an equation of the form (??). Suppose for some time $t_1$, for all stimuli u(t) that advance θ from θ (0)=0 to θ($t_1$)=ω$t_1$ (that is, stimuli that do not create any net change of phase), we want to find the stimulus that minimizes the cost function $G[u(t)]=\int_0^{t_1}[u(t)^2-\beta Z'(\theta(t))u(t)]dt$. Here, $\int_0^{t_1}[u(t)^2]dt$ corresponds to the power associated with the stimulus, and β>0 is a scaling parameter that determines the relative importance of minimizing the energy versus maximizing the Lyapunov exponent, Λ($t_1$). We apply calculus of variations to minimize $$C[u(t)] = \int_0^{t_1} \left\{ u(t)^2 - \beta Z'(\theta)u(t) + \lambda\left(\frac{d\theta}{dt} - \omega - Z(\theta)u(t)\right) \right\} dt, \quad (5)$$

where the Lagrange multiplier λ forces the neural dynamics to obey equation (??). The resulting Euler-Lagrange equations are $$u(t)=[\beta Z'(\theta)+\lambda Z(\theta)]/2, \quad (6)$$

$$\dot{\theta}=Z(\theta)[\beta Z'(\theta)+\lambda Z(\theta)]/2+\omega, \quad (7)$$

$$\dot{\lambda}=-[\beta Z'(\theta)+\lambda Z(\theta)][\beta Z''(\theta)+\lambda Z'(\theta)]/2, \quad (8)$$

where '=d/dθ. To find the optimal control, u(t), equations (??) and (??) must be solved subject to the boundary conditions θ(0)=0, θ($t_1$)=ω$t_1$. This can be done by numerically finding the initial condition λ(0)≡$\lambda_0$ that satisfies the boundary conditions, for example, by using a shooting method. We note that the above conditions are only necessary and not sufficient for global optimality. However, the phase reduction (??) requires inputs of small amplitude so that solutions remain close to the periodic orbit. Since u(t) is directly proportional to λ in equation (??), we can limit our search to include solutions obtained with reasonably small values of λ(0) in order to find a feasible solution.

While the previous procedure described supra will produce an energy-optimal stimulus, it will not necessarily be charge-balanced (CB). The importance of CB stimuli in DBS has been known for many years. Over time, non-charge-balanced (NCB) stimuli can create an accumulation of charge and cause harmful Faradaic reactions that may damage surrounding neural tissue or the DBS electrode. If we consider the total charge q imparted to a neuron to be the integral of the current, then $\dot{q}(t)=Cu(t)$, and we can derive an optimal CB stimulus by optimizing the same cost function as in the NCB case, G[u(t)], subject to the additional constraints q(0)=0 and q($t_1$)=0, the latter ensuring that the stimulus will be charge neutral at $t_1$. We again apply calculus of variations to minimize C[Φ(t), $\dot{\Phi}$(t), u(t)]=$\int_0^{t_1}$M[u(t)]dt where $$M[u(t)] = u(t)^2 - \beta Z'(\theta)u(t) + [\lambda_1(t) \quad \lambda_2(t)] \begin{bmatrix} \frac{d\theta}{dt} - \omega - Z(\theta)u(t) \\ \frac{dq}{dt} - u(t) \end{bmatrix}, \quad (9)$$

and Φ(t)=[θ(t), q(t), $\lambda_1$(t), $\lambda_2$(t)]$^T$. The Lagrange multipliers $\lambda_1$ and $\lambda_2$ force the dynamics to satisfy the evolution equations for θ and q given above. The associated Euler-Lagrange equations are $$\frac{\partial M}{du} = \frac{\partial}{dt}\left(\frac{\partial M}{d\dot{u}}\right), \frac{\partial M}{d\Phi} = \frac{\partial}{dt}\left(\frac{\partial M}{d\dot{\Phi}}\right). \quad (10)$$

With the above boundary conditions, this is a two-point boundary value problem for u(t) which is solved using a double bisection algorithm. As with the NCB formulation, (??) is only necessary and not sufficient for global optimality, but we can limit our search for $\lambda_1$(0) and $\lambda_2$(0) so that the resulting solutions yield optimal stimuli that are small enough so that the phase reduction (??) is still valid.

Robustness of Waveform Design

In an experimental setting, errors in measuring the PRC will induce errors in the calculated optimal stimulus. An important question to ask is whether or not these errors will stifle the desynchronizing efforts of the electrical signal, and how large these errors need to be before they completely degrade its desynchronizing capabilities. To answer these questions, we considered an NCB optimal stimulus, $I_{opt}$(t), found using methods described supra. Consider another stimulus $I_c$(t) that is different from $I_{opt}$(t). We define the error signal as $I_e$(t)=$I_c$(t)-$I_{opt}$(t) and the infinity norm of $I_e$(t) as $$\|I_e(t)\|_\infty = \sup_{0 \leq t \leq t_1} |I_e(t)|, \quad (11)$$

where $t_1$ is the duration of the optimal signal. As we will demonstrate infra, a signal with a larger Lyapunov exponent will desynchronize two neurons with similar initial phase more quickly. For this reason, we use the Lyapunov exponent from (??) as a measure of the desynchronizing capabilities of a signal. To identify a bound on $\|I_e(t)\|_\infty$ which can guarantee desynchronization, we must find the worst possible Lyapunov exponent for any signal with $\|I_e(t)\|_\infty \leq E$, where E is a constant. To do so, we define the cost function $\mathcal{L}[I_e(t)]=\int_0^{t_1}[I_{opt}(t)+I_e(t)]Z'(\theta(t))dt$ subject to (??), $\dot{\theta}=\omega+Z(\theta)[I_{opt}(t)+I_e(t)]$, with the additional constraint $-E \leq I_e(t) \leq E$ for all t ∈ [0, $t_1$]. Here, $\mathcal{L}[I_e(t)]$ corresponds to the Lyapunov exponent for a stimulus $I_c$(t). The inequality constraint ensures that $\|I_e(t)\|_\infty \leq E$. Using Pontryagin's Minimum Principle, a necessary condition for the control that minimizes $\mathcal{L}[I_e(t)]$ is that the control minimizes the Hamiltonian $$H(\theta(t), I_e(t), p_1(t)) = [I_{opt}(t)+I_e(t)]Z'(\theta(t))+\omega p_1(t)+[I_{opt}(t)+I_e(t)]p_1(t)Z(\theta(t)), \quad (12)$$

and is given by $I_e$(t)=-Esign(Z'(θ)+$p_1$(Z(θ))) where '=d/dθ, and $p_1$ is a Lagrange multiplier. Furthermore, $$\dot{\theta}=\omega+Z(\theta)[I_{opt}(t)+I_e(t)], \quad (13)$$

$$\dot{p}_1=-[I_{opt}(t)+I_e(t)]Z''(\theta)-p_1Z'(\theta)[I_{opt}(t)+I_e(t)], \quad (14)$$

with the boundary condition θ(0)=0. From the problem formulation, we only have one boundary condition, and to find the global minimum of $\mathcal{L}[I_e(t)]$, we must simulate equations (??) and (??) for all plausible values for $p_1$(0) to determine the minimum (worst case) Lyapunov exponent of the associated signals. Using this approach, we can find boundaries on a stimulus that are sufficient, but not necessary, to yield a given Lyapunov exponent.

Optimal Control of the Phase Distribution

The methods described supra are optimal for desynchronizing two neurons with close initial phase. However, brain regions can contain on the order of billions of neurons. For large populations of neurons, rather than examining individual neurons, which can be too large to simulate in silico, it is appropriate to monitor the probability density of neurons with phase θ at a given time, ρ(θ, t). For an uncoupled population that obeys equation (??), the probability density evolves according to the advection equation:

$$\frac{\partial \rho(\theta, t)}{\partial t} = -\frac{\partial}{\partial \theta}[\{\omega + Z(\theta)u(t)\}\rho(\theta, t)] = -\rho \frac{\partial v}{\partial \theta} - v \frac{\partial \rho}{\partial \theta}, \quad (15)$$

where v(θ, t)=ω+Z(θ)u(t). As described above, we show that the CB and NCB optimal signals obtained using methods above can effectively desynchronize a network of 100 coupled neurons for many different neural models. Therefore, it is no surprise that the same signal is effective at desynchronizing a population evolving according to (??) (not shown).

However, we wish to approach this problem from a neural population perspective, to see if we can find an effective control strategy to desynchronize large neural populations. Suppose we are interested in the evolution of the maximum of the distribution, $\rho_M$, at $\theta \equiv \theta_M$. Noting that the total time derivative of the distribution is $$\frac{d\rho}{dt} = \frac{\partial \rho}{\partial t} + \frac{\partial \rho}{\partial \theta}\frac{d\theta}{dt},$$

and that $$\frac{\partial \rho}{\partial \theta} = 0$$

at the local maximum, we find $$\frac{d\rho_M}{dt} = -\rho_M \frac{\partial v}{\partial \theta}(\theta_M, t) = -Z'(\theta_M)u(t)\rho_M. \quad (16)$$

Note the similarity of (??) to equation (??). From the two-neuron optimal control formulation, Z'(θ)u(t)>0 corresponds increasing the phase difference, whereas here, it corresponds to a decreasing value of $\rho_M$. In order to find an equation for the evolution of $\theta_M$, we again make use of the relation $$\frac{\partial \rho}{\partial \theta}\bigg|_{\theta_M} = 0.$$

Taking the total time derivative yields $$0 = \frac{\partial}{\partial \theta}\frac{d\rho}{dt}, \quad (17)$$

$$= \frac{\partial}{\partial \theta}\left[\rho_\theta \frac{d\theta_M}{dt} + \rho_t\right],$$

$$= \frac{\partial}{\partial \theta}\left[\rho_\theta \frac{d\theta_M}{dt} - v_\theta \rho - \rho_\theta v\right],$$

$$\rho_{\theta\theta}\frac{d\theta_M}{dt} = v_{\theta\theta}\rho + 2v_\theta \rho_\theta + \rho_{\theta\theta}v.$$

All expressions in the above equation are evaluated at $\rho_M$ and $\theta_M$, thus $\rho_\theta=0$. Also, since $\rho_M$ is a local maximum, $\rho_{\theta\theta}<0$, and equation (??) becomes $$\frac{d\theta_M}{dt} = \omega + Z(\theta)u(t) + \frac{\rho_M}{\rho_{\theta\theta}}Z''(\theta)u(t). \quad (18)$$

To effectively use (??), we must find some function $\kappa(\theta_M, \rho_M)\approx\rho_{\theta\theta}$. One such κ, which works well in practice, can be obtained by starting with a Gaussian distribution and assuming that the distribution remains Gaussian for all time. We note that while the phase reduction is valid for θ ∈ [0, 2π), a Gaussian distribution is defined for all θ. However, because we are considering synchronized systems with a small variance, the values of the Gaussian distribution that we are ignoring are insignificant. Using this strategy, one can easily show that $\kappa(\rho_M)=-2\pi\rho_M^3$.

Equation (??) is separable, and we can solve explicitly to determine the change in the value of ρ over some time interval of length T $$\int_a^{a+T} \frac{1}{\rho_M} d\rho_M = \quad (19)$$

$$-\int_a^{a+T} Z'(\theta_M)u(t)dt, \Rightarrow \log\left(\frac{\rho_M(a+T)}{\rho_M(a)}\right) = -\int_a^{a+T} Z'(\theta_M)u(t)dt.$$

If we want to minimize $\rho_M$ while taking into account the energy expended, we can use calculus of variations to minimize C[Φ(t), Φ̇(t), u(t)]=$\int_0^{t_1}$G[u(t)]dt where $$\mathcal{G}[u(t)] = u(t)^2 - \beta Z'(\theta_M)u(t) + [\lambda_1(t) \; \lambda_2(t)] \quad (20)$$

$$\begin{bmatrix} \frac{d\theta}{dt} - \omega - Z(\theta)u(t) - \frac{\rho_M}{\kappa(\theta_M, \rho_M)}Z''(\theta)u(t) \\ \frac{d\rho_M}{dt} + \rho_M Z'(\theta)u(t) \end{bmatrix},$$

and Φ(t)=$[\theta_M(t), \rho_M(t), \lambda_1(t), \lambda_2(t)]^T$. Lagrange multipliers $\lambda_1$ and $\lambda_2$ force the dynamics to satisfy (??) and (??). Note the similarity of (??) to the NCB cost function (??). When $\kappa(\theta_M, \rho_M) \gg \rho_M Z''(\theta)u(t)$ (as might be the case for a highly synchronized network) the function that minimizes (??) is approximately the same function that minimizes (??). Taking $\kappa(\rho_M)=-2\pi\rho_M^3$ as previously mentioned, the associated Euler-Lagrange equations are $$u(t) = \left[\beta Z'(\theta_M) + \lambda_1\left(Z(\theta_M) - \frac{1}{2\pi\rho_M^2}Z''(\theta_M)\right) - \lambda_2 \rho_M Z(\theta_M)\right]/2, \quad (21)$$

$$\dot{\rho_M} = -\rho_M Z'(\theta_M)u(t), \quad (22)$$

$$\dot{\theta_M} = \omega + Z(\theta_M)u(t) - \frac{1}{2\pi\rho_M^2}Z''(\theta_M)u(t), \quad (23)$$

$$\dot{\lambda_1} = \lambda_1 u(t)\left[\frac{1}{2\pi\rho_M^2}Z'''(\theta_M) - Z'(\theta_M)\right] + Z''(\theta_M)u(t)[\rho_M \lambda_2 - \beta], \quad (24)$$

$$\dot{\lambda_2} = u(t)\left[-\frac{\lambda_1 Z''(\theta_M)}{\pi\rho_M^3} + \lambda_2 Z'(\theta_m)\right]. \quad (25)$$

Unlike the problem for finding the maximum Lyapunov exponent, the distribution minimization problem depends on the initial height of the distribution, $\rho_M(0)$. We will take $\theta_M(0)=0$ which leaves two initial conditions to be determined later.

Results and Discussion
Maximizing Lyapunov Exponents for the Thalamus Model

Because pathological neural synchronization in the thalamus is thought to play an important role in Parkinson's disease, we consider a three-dimensional model to describe thalamic neural activity:

$$\dot{V}_i = \left(-I_L(V_i) - I_{Na}(V_i, h_i) - I_K(V_i, h_i) - I_T(V_i, r_i) + I_{SM} + \frac{1}{N}\sum_{i=1}^{N}\alpha_{ij}(V_j - V_i) + u(t) + \eta_i(t)\right)\Big/C, \quad (26)$$

$$\dot{h}_i = (h_\infty(V_i) - h_i)/\tau_h(V_i),$$

$$\dot{r}_i = (r_\infty(V_i) - h_i)/\tau_r(V_i), i = 1, \ldots, N.$$

We have augmented the voltage equation by additively including electrotonic coupling, DBS input, and Gaussian white noise. Here, N is the total number of neurons, $V_i$, $h_i$, and $r_i$ are membrane voltage and gating variables for neuron i, $\alpha_{ij}$ characterizes the coupling strength between electrotonically coupled neurons i and j, with $\alpha_{ij}=\alpha_{ji}$ and $\alpha_{ii}=0$ for all i, $\eta_i(t)=\sqrt{2D}N(0, 1)$ is the i.id. noise associated with each neuron, assumed to be zero-mean Gaussian white noise with variance 2 D, and u(t)=I(t)/C represents a common control input. In this equation $I_{SM}$ represents the baseline current which we take to be 5 μA/cm². For a full explanation of the functions $I_L$, $I_{Na}$, $I_K$, $I_T$, $h_\infty$, $\tau_h$, $r_\infty$ and $\tau_r$, we refer the reader to J. Rubin and D. Terman. High frequency stimulation of the subthalamic nucleus eliminates pathological thalamic rhythmicity in a computational model. Journal of Computational Neuroscience, 16:211235, 2004.

The baseline current causes the neuron to fire with period T=8.395 ms. To obtain the optimal control, we take $t_1$=7.35 ms (corresponding to θ=5.5 on the limit cycle) and β=40. Note that $t_1$ sets the duration of the stimulus, and could be chosen differently provided that it is sufficiently smaller than T, and β has been chosen so that a positive Lyapunov exponent is favored, but that the magnitude of the control input is small enough so that the phase reduction from equation (??) is still valid. We solve equations (??) and (??) numerically with a fourth order Runge-Kutta solver and the optimal control is found from (??). We do the same for the Euler-Lagrange equations from (??).

Panels A and B of FIGS. 2A-B show the PRC and its first derivative for (??), numerically obtained using the software X-Windows Phase Plane (XPP). Panel C of FIG. 2-C shows the optimal CB and NCB stimuli. Both stimuli are similar because the NCB stimulus is nearly charge-balanced. We note that the optimal stimulus is strikingly similar to Z'(θ) for θ≤5.5 and explain this occurrence by noting that the equation for the optimal stimulus from (??) depends directly on the sum of βZ'(θ(t)) and λ(t)Z(θ(t)). The optimal stimulus has a relatively small magnitude, so θ(t)≈ωt and, numerically, we find that λ(t) is relatively small compared to β.

Figure 3:
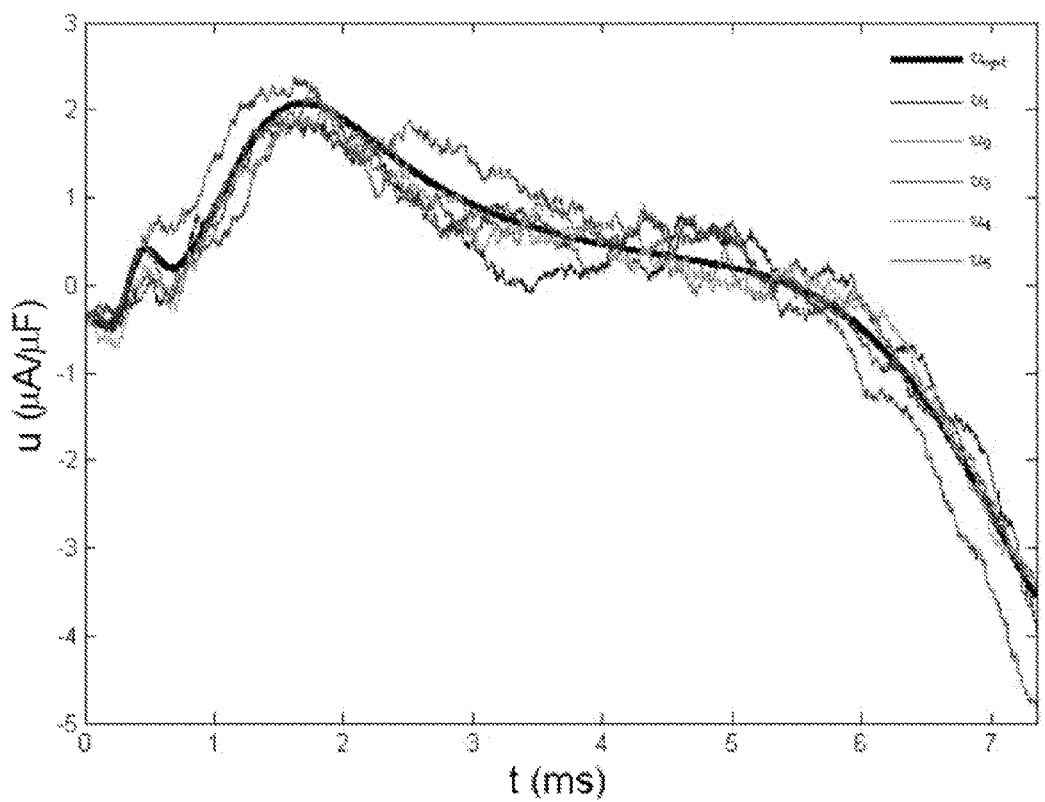
FIG. 3 shows according to an exemplary embodiment of the invention the NCB optimal stimulus $u_{opt}$ and 5 instances of $u_{opt}$ that have been corrupted by noise. Indeed, out of the 5 stimuli, $u_{opt}$ defines the smallest value of C[u(t)], but the other stimuli give values that are close to optimal.

To numerically verify that the NCB stimulus is optimal for minimizing the cost function, we analyze five other stimuli given by $u_i(t)=u_{opt}(t)+0.5 W_i(t)$, i=1 . . . 5 where $u_{opt}$ is the optimal NCB stimulus shown in FIGS. 2-A-C , and IV, is a Wiener process, added to corrupt the optimal stimulus. We note that each of these stimuli are subject to the same end point conditions described above. FIG. 3 shows these stimuli as well as the NCB optimal stimulus for reference. We find that $u_{opt}$ does have the best performance in terms of overall cost, but the other stimuli still yield comparable Lyapunov exponents. This prompts the question of how robust this procedure is to errors, which will be addressed later.

TABLE 1

| | Stimulus properties from FIG. 3 | | |
|---|---|---|---|
| stimulus | Λ (T) | Energy | C[u(t)] |
| $u_{opt}$ | 0.066 | 11.66 | −10.43 |
| $u_1$ | 0.055 | 8.80 | −9.68 |
| $u_2$ | 0.062 | 10.7 | −10.03 |
| $u_3$ | 0.058 | 9.66 | −9.89 |
| $u_4$ | 0.061 | 10.44 | −10.06 |
| $u_5$ | 0.086 | 19.98 | −8.95 |

The Lyapunov exponents calculated using equation (??) for NCB and CB stimuli are 0.066 and 0.060 respectively. We find that requiring the CB constraint decreases the Lyapunov exponent, and hence, the rate of desynchronization. FIGS. 4-A-D show the phase separation of two neurons which obey equation (??) for the PRC found in FIGS. 2A-C subject to repeated iterations of both the NCB (Panels A and B) and CB (Panels C and D) stimuli. We find that the neurons exponentially desynchronize at a rate determined by their Lyapunov exponent until they are nearly π radians out of phase. At this point, the assumption that the neurons are close in phase is no longer valid, and no further desynchronization occurs.

Results from FIGS. 4A-D only apply to neurons obeying the phase reduction (??). To determine the validity of the phase reduction for (??), we simulate the deterministic version of equations (??), i.e. with D=0, using a fourth order Runge-Kutta solver. The top panel of FIGS. 5A-B shows time histories of three neurons with initial conditions that correspond to θ=−0.1, 0, and +0.1. on the periodic orbit. The control is applied every time the reference neuron, with initial phase θ=0, fires. We find that after 70 ms, the neurons no longer show any evidence of their initial synchronization.

We now apply the NCB optimal control found above to a network of N=100 coupled, initially synchronized, noisy neurons, with an identical coupling strength of $\alpha_{ij}$=0.1 and i.i.d. noise with D=1, to test the desynchronizing effects on the full neural model. We define the mean voltage as our system observable, $\overline{V}(t)=1/N\Sigma_{i=1}^{N}V_i(t)$, The controller has two states: active and inactive. When the controller is active, a new stimulus is triggered when $\overline{V}$>−45 mV and $\overline{\dot{V}}$<0 with the caveat that a new stimulus cannot occur until the previous stimulus is either finished, or within 0.3 ms of finishing. This last condition is included to give the controller flexibility in when to start the next stimulus because the system is sensitive to the time when the stimulus is presented. Once $\overline{V}$ no longer spikes above −45 mV, the controller changes to an inactive state. It changes back to the active state if $\overline{V}$ registers above −40 mV. We use the algorithm presented in Honeycutt 1992 (R. Honeycutt. Stochastic Runge-Kutta algorithms. I. white noise. Physical Review A, 45:600 603, 1992) to simulate the noisy system (see FIGS. 6A-D), however other control logic would also work. The desynchronizing effect of the stimulus can clearly be seen in the raster plot. We call this event-based control because the controller is only triggered when the mean voltage crosses a certain threshold. It is worth noting that the optimal stimulus works equally well for a network of neurons that are synchronized by a common pulsatile input, which is suggested to be the mechanism that yields synchronization.

The critical advantage of using this control strategy is that it only requires knowledge of the PRC for the system. Methods for controlling neurons that require precise knowledge of the neural model are difficult to implement because, despite recent progress, it is challenging to obtain accurate full scale models of real neurons for control purposes. Methods that rely on the PRC are attractive because it is experimentally measurable. To illustrate the effectiveness of this method, we employ the following method which we will refer to as the direct method to obtain a PRC for a single neuron obeying equation (??). To obtain one data point, a short-duration pulse of current is applied to a neuron at a random phase θ, and the resulting phase change is measured by observing the change in spike time. The resulting value Z(θ) is $$\frac{\Delta\theta}{Q_P/C}$$

where $Q_p$ is the total charge imparted to the neuron from the pulse, and $\Delta\theta$ is the change in phase. An experimentally reasonable sampling size of 300 data points were obtained for noise levels of both D=1 and 0.25, and the data was fit to a $6^{th}$ order polynomial constrained to be zero at both θ equals 0 and 2π. The results are shown in panel A of FIG. 7A. As expected, a larger noise value yields a larger spread in the data, and a less reliable PRC. The optimal stimuli obtained using the fit PRC are shown in panel B. Finding the PRC with a D value of 0, 0.25, and 1 yields an optimal stimulus with Λ=0.066, 0.055, and 0.046, respectively. When we do not know the PRC exactly, the performance of the desynchronizing stimulus is somewhat degraded as evidenced in panels C, and D, but the stimulus still performs remarkably well. We note that for a noise level of D=1, the spread in the collected data for the PRC is similar to data previously collected for in vitro neurons.

FIGS. 7A-D show results from a simulation using the optimal stimulus obtained from this data applied to 100 coupled neurons obeying equation (??) with the same noise and coupling parameters as the test shown in FIGS. 6A-D. The stimulus still shows desynchronizing capabilities similar to the stimulus obtained from the true PRC.

To model more realistic neural networks, we include network heterogeneities. For comparison, our homogeneous network simulations will use N=100, $\alpha_{ij}$=0.1 and $I_b$=5. Other simulations will consider network heterogeneities in coupling strength by drawing $\alpha_{ij}$ values from a normal distribution with mean $\bar{\alpha}$=0.1 and a standard deviation $\sigma_\alpha$=0.02; panel A of FIG. 9A shows the specific distribution used for each simulation. Network heterogeneities in $I_b$ are also considered by simulating a system with baseline currents drawn from a normal distribution (shown in panel B of FIG. 9A). In each N=100 neuron simulation, we use the same control logic as the simulation with results shown in FIGS. 7A-D to determine when to apply each new stimulus. Again, we use the algorithm presented in Honeycutt (1992; R. Honeycutt. Stochastic Runge-Kutta algorithms. I. white noise. Physical Review A, 45:600 603, 1992) to simulate the noisy system.

Results of each simulation are shown in FIGS. 10A-D. The top panel shows the result for the network with homogeneous baseline current and coupling. The second panel shows results for a neural network with homogeneous baseline currents $I_b$=5 and coupling strengths drawn from a random distribution (shown in panel A of FIG. 9A) and the third panel shows results for a network with homogeneous coupling $\alpha_{ij}$=0.1 and baseline currents drawn from a random distribution (shown in panel B of FIG. 9B). We find that when we include heterogeneity the network requires fewer applications of the optimal stimulus to desynchronize. The bottom panel shows results for a network with both heterogeneous coupling and baseline currents. Overall, we find that heterogeneity in a network decreases its tendency to resynchronize, which increases the effectiveness of the optimal control.

Clearly the optimal stimulus works well for desynchronizing a neural network, even when only an approximation to the true PRC is known. This prompts the search for error bounds on the optimal stimulus that can still guarantee desynchronization. In an ad hoc manner using methods described supra, we fix a particular value of E for the signal $I_e$ and minimize (??) to find the minimal (worst case) Lyapunov exponent. We then simulate (??) to with the associated signal to determine if it can affect network desynchronization. Using this strategy with different E values, we find that for a network of 100 neurons with homogeneous coupling $\alpha_{ij}$=0.1 and baseline current, $I_b$=5 μA/cm² we require a Lyapunov exponent of at least, Λ=0.024, corresponding to E=0.8, to achieve sufficient desynchronization so that spikes of $\bar{V}$ remain below −40 mV. Thus, $\|I_e(t)\|_\infty \leq 0.8$ will guarantee Λ≥0.024. To illustrate the utility of this measure, we choose a simple, piecewise linear signal which is nearly contained entirely in the boundary $\|I_e(t)\|_\infty \leq 0.8$.

$$u(t) = \begin{cases} t, & 0 \leq t \leq 2.2 \\ -4.4 - t, & 2.2 < t \leq 7.35 \end{cases}. \quad (27)$$

The signal in (??) is used in a simulation of the same homogeneous network with the same control logic described previously. The results are shown in FIGS. 11A-C. Numerically, we find the Λ=0.0577 for this stimulus. We note that even though the stimulus is not entirely contained within the shaded region shown in the top panel of FIGS. 11A-C, and therefore, not guaranteed to desynchronize the system, it still produces a sufficiently high Lyapunov exponent to achieve desynchronization.

Optimally Decreasing the Peak of a Distribution for the Thalamus Model

We now turn our attention to controlling populations of neurons using the methods described herein to optimally decrease the peak of their phase distribution. Here, we attempt to provide reasonable values for the still undetermined parameters in the Euler-Lagrange Equations (??)-(??). Because we have undetermined parameters, we cannot claim to have found an optimal stimulus to minimize our cost function, but we can still gather powerful insight about stimuli that will affect network desynchronization. To make explicit comparisons with the optimal stimulus which maximizes the Lyapunov exponent, we take $t_1$=7.35ms and β=40. We take our initially synchronized distribution to be a normal distribution with standard deviation $\sigma_d$=0.2 centered at θ=0, which corresponds to a spiking event. These conditions were chosen as a reasonable approximation of the observed distribution for simulations of network (??) just before the control threshold $\bar{V}$=−40 mV is reached. This gives $\theta_M(0)$=0 and $\rho_M(0)$=1.995 as initial conditions to (??) and (??); however, we still need to determine $\lambda_1(0)$ and $\lambda_2(0)$. In order to find the best choice of the remaining initial conditions, we minimize the cost function for reasonable choices of $\lambda_1(0)$ and $\lambda_2(0)$. Using this approach we find $\lambda_1(0)$=18 and $\lambda_2(0)$=2 approximately minimizes the cost function, and gives the stimulus shown in FIG. 12, which will be referred to as $u_D$.

We apply $u_D$ to (??) and (??) with N=250, D=0 and $\alpha_{ij}$=0 to determine the validity of the results found using the phase reduction. Throughout the simulation, we infer the phase of each of neuron in (??) by simulating each neuron separately in the absence of DBS input and noise to determine when its next spiking event occurs. FIGS. 13A-C show three frames from this animation. To clearly present the results, the mapping $\theta \in (\pi, 2\pi) \rightarrow (-\pi, 0)$ is used, e.g., $$\theta = \frac{3\pi}{2}$$

is plotted as $$\theta = -\frac{\pi}{2}.$$

Theoretical and numerical evolutions are shown in black and grey areas, respectively. Theoretical evolution of the distribution in the absence of stimulus and is shown for reference as a grey line. Throughout the simulation, the dynamics of the 250 neuron system is well approximated by (??), and the optimal stimulus brings $\rho_M$ from 1.995 to 0.776. We now see utility of the approach which minimizes the peak of the distribution compared to an approach which maximizes the NCB Lyapunov exponent (producing a stimulus we will refer to as $u_A$). From (??), we see that a stimulus has the potential to greatly decrease a distribution when $|Z'(\theta_M)|$ is relatively large. For the Thalamus model, this can be done by applying a large negative stimulus when $\theta_M \approx 5.8$. As shown in FIG. 12, $u_D$ and $u_A$ are nearly identical for $0 \le t < 2$ but from about $2 \le t < 6$, $u_D > u_A$ at a time when $Z(\theta_M) > 0$ and $Z'(\theta_M) \approx 0$. This has the effect of speeding up the distribution, but not decreasing the peak height. The extra effort used in speeding up the peak is repaid when $\theta_M \approx 5.8$, when a large negative stimulus decreases the peak rapidly at a time when $Z'(\theta) < 0$. The distribution deforms in such a way that $\rho_M$ remains at $\theta_M \approx 5.8$ longer than we would expect for a system of only two neurons, which is reflected in the inequality $u_D < u_A$ for $t \approx 6$.

We have found stimuli for desynchronizing neural networks using two different approaches. Both approaches produce similar results, but we would like to know if one is better than the other. To answer this question, we simulate (??) with N=250, D=1, and $\alpha_{ij}$=0.1 for 1000 ms using the same control strategy as the simulations from FIGS. 10A-D. The initial phase distribution is drawn from a normal distribution with $\sigma_d$=0.2 centered at $\theta$=0. A representative portion of the comparison is shown in FIGS. 14A-D. When we use $u_D$ as the control, the overall energy use is 533 units, while for $u_A$, the energy consumption is 460 units. In terms of energy, $u_D$ performs slightly worse than $u_A$, most likely because the neuron distribution is not quite Gaussian throughout the simulation as we had assumed to derive $u_D$, but both strategies yield an effective control input using a comparable amount of energy. We also note that $u_D$ desynchronizes the network more quickly than $u_A$, which is expected because it has a higher Lyapunov exponent than $u_D$ as calculated from (??), $\Lambda$=0.107 and 0.066, respectively, but requires more energy per application of the stimulus.

Maximizing Lyapunov Exponents for the Reduced Hodgkin-Huxley Model

We next apply our optimization method to a population of neurons, each described by a two-dimensional reduction of the renowned four-dimensional Hodgkin Huxley (HH) model that reproduces the essential characteristics of a neuron's dynamical behavior. The population of neurons is modeled as follows:

$$\dot{V}_i = f_V(V_i, n_i) + \frac{1}{N}\sum_{i=1}^{n} \alpha_{ij}(V_j - V_i) + u(t) + \eta_i(t), \quad (28)$$

$$\dot{n}_i = f_n(V_i, n_i).$$

Here, i=1, ..., N where N is the total number of neurons, $V_i$ and $n_i$ are membrane voltage and gating variables for neuron i, $\alpha_{ij}$ characterizes the coupling strength between electrotonically coupled neurons i and j, with $\alpha_{ij}=\alpha_{ji}$ and $\alpha_{ii}=0$ for all i, $\eta_i(t) \in \sqrt{2D}N(0,1)$ is the noise associated with each neuron, assumed to be zero-mean Gaussian white noise with variance 2 D, u(t)=I(t)/C represents a common control input where I(t) is a DBS input current in $\mu A/\mu F$, and C=1 $\mu F/cm^2$ is the membrane capacitance. Furthermore, $$f_V = (I_b - \bar{g}_{Na}[m_\infty(V)]^3(0.8-n)(V-V_{Na}) - \bar{g}_K n^4 (V-V_k) - \bar{g}_L(V-V_L))/C,$$

$$f_n = a_n(v)(1-n) - b_n(V)n.$$

Other functions and parameters for the reduced model are $$m(V) = \frac{a_m(V)}{a_m(V) + b_m(V)},$$

$$a_m(V) = 0.1(V+40)/(1-\exp(-(V+40)/10)),$$

$$b_m(V) = 4\exp(-(V+65)/18),$$

$$a_n(V) = 0.01(V+55)/(1-\exp(-(V+55)/10)),$$

$$b_n(V) = 0.125\exp(-(V+65)/80),$$

$$V_{Na} = 50 \text{ mV}, V_K = -77 \text{ mV}, V_L = -54.4 \text{ mV},$$

$$\bar{g}_{Na} = 120 \text{ mS/cm}^2, \bar{g}_K = 36 \text{ ms/cm}^2,$$

$$\bar{g}_L = 0.3 \text{ mS/cm}^2, c = 1 \text{ }\mu F/cm^2,$$

$$I_b = 10 \text{ }\mu A/cm^2.$$

Here, $\bar{g}_{Na}$, $\bar{g}_K$, and $\bar{g}_L$ represent the conductances of the sodium, potassium and leakage channels, respectively, and $V_{Na}$, $V_K$, and $V_L$ are their respective reversal potentials. Note that $I_b$, the neuron's baseline current, represents the effect of the surrounding brain regions on the neuron. This is a bifurcation parameter, with the value $I_b$=10 $\mu A/cm^2$ chosen to ensure that the neuron is in an oscillatory (periodically spiking) regime. The natural period, T of oscillation is 11.81 ms.

The PRC, $Z(\theta)$, for this system is computed numerically with the software X-Windows Phase Plane (XPP) and is shown in FIGS. 15A-C. To perform computations with the PRC, we approximate it as a Fourier series with 1200 terms. We take this many terms to get a reasonably non-oscillatory estimate of $Z'''(\theta)$ when solving (??).

The bottom panel C of FIGS. 15A-C shows the result of the optimization process with and without the charge-balanced constraint for the choice of parameters $t_1$=10.34 ms (corresponding to $\theta$=5.5 on the limit cycle) and $\beta$=9. Note that $t_1$ sets the duration of the stimulus and could be chosen differently provided that it is sufficiently smaller than the natural period, T, of the neuron, and $\beta$ is chosen so that a positive Lyapunov exponent is favored, but the magnitude of the control input will be small enough so that the phase reduction is still valid. We find that the CB stimulus looks nearly identical to the NCB stimulus except for a downward shift. This is to be expected since, as is the case in the Thalamus model, the NCB stimulus is nearly charge balanced. Also, we find that the optimal control looks similar to the derivative of the PRC as shown in FIGS. 15A-C.

Figure 15:
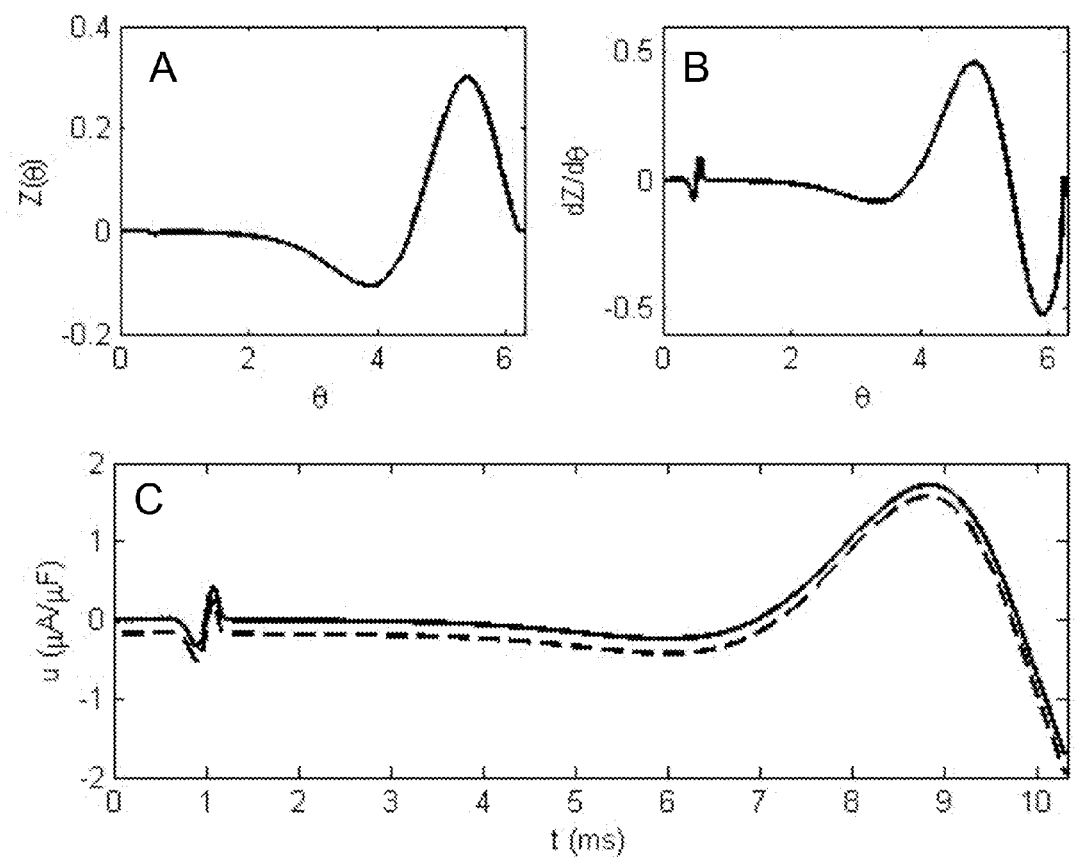
Figure 16:
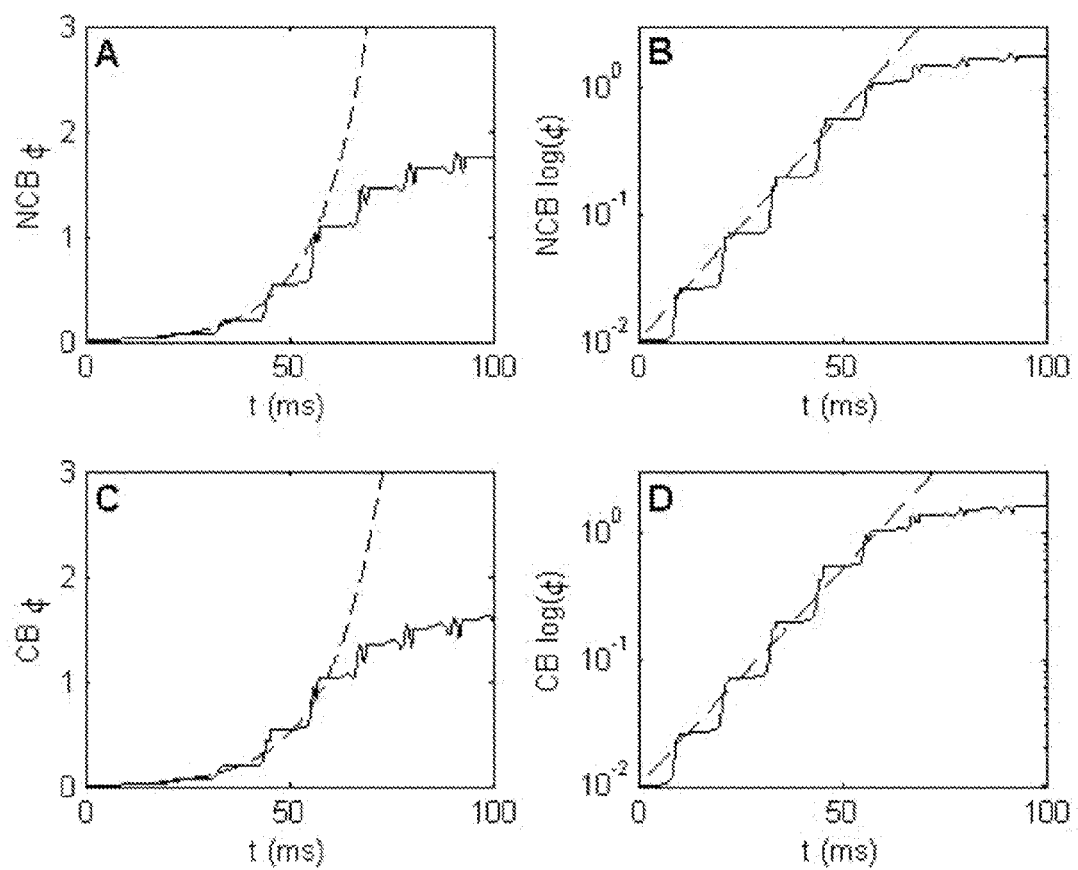

Panels A and B in FIGS. 16A-D show the phase difference between two neurons with nearly identical initial phases, subject to the NCB optimal stimulus as shown in FIGS. 15-A-C. The optimal stimulus is event-based, and is applied every time the phase of the trailing neuron crosses θ=0. Panels C and D show the results of a similar test with the CB stimulus. The Lyapunov exponents, Λ, for the NCB and CB stimuli are found to be 0.0823, and 0.0782, respectively. Dashed lines show exponential functions based on the Lyapunov exponents. We find that all of the plots match closely until φ≈1, with the NCB stimulus performing slightly better than the CB stimulus. In this case, balancing charge comes at the cost of degrading performance.

It is natural to wonder to what degree the optimal control found from the phase model will desynchronize neurons that obey the set of equations with which we started. To this end, we simulate the deterministic version of equations (??), i.e., with D=0, using a fourth order Runge-Kutta solver. The top panel A in FIGS. 17A-B shows the time histories of three neurons with initial conditions that correspond to θ=−0.1, 0, and +0.1 on the periodic orbit. The control is applied every time the reference neuron, with initial phase θ=0, fires. FIGS. 17A-B also shows the input for reference. We find that after 90 milliseconds, the neuron that started at θ=+0.1 now fires approximately 6 milliseconds after the reference neuron, while the neuron that starts at θ=−0.1 fires approximately 2 milliseconds before the reference neuron. The reason for this discrepancy can be explained by noting shape of the PRC. We see in FIGS. 15A-C, the PRC has a local minimum at θ≈4. After approximately 9 ms after the optimal stimulus is first presented, the remaining stimulus has negative sign, the reference neuron has a phase corresponding to a positive value on the PRC, and the neuron which starts behind has a phase of θ≈4. Because of these conditions near the end of the cycle, the optimal stimulus to brings the phases closer together, negating the desynchronization achieved earlier in the cycle.

We now apply this optimal control to a network of N=100 coupled, initially synchronized, noisy neurons, with an identical coupling strength of $\alpha_{ij}$=0.05 and i.i.d. noise with D=0.7. The control logic used is similar to the logic presented supra, with the controller switching to the inactive state if spikes remain below −40 mV and switching back to the active state if a spike registers above −30 mV.

FIGS. 18A-D show the result of this simulation. The top panel shows voltages of each neuron as well as the average voltage of the coupled, noisy system without control. We find that $\overline{V}$ peaks near 0 mV throughout the simulation, and the neurons stay synchronized. The second panel shows the individual neuron voltages and mean voltage for the same coupled system with both noise and control input. The horizontal line in this panel represents the threshold voltage of −30 mV. The control input is shown in the third panel. Clearly the control input desynchronizes the network of neurons, as seen from the raster plot, and since the control is event-based, it only needs to be turned on once $\overline{V}$ crosses the threshold line.

In an experimental setting, it is unlikely that the optimal desynchronizing stimulus $I_{opt}(t)$ can be found exactly. For this reason, we would like to calculate bounds on $I_e(t)$, where $I(t)=I_{opt}(t)+I_e(t)$ with I(t) found using an experimentally obtained PRC such that we can guarantee a given Lyapunov exponent. Using the strategy developed and described supra, we can determine a worst case Λ for a particular $\|I_e\|_\infty$. Here, we use a shooting method to determine that in order to guarantee stimuli with Λ≥0.06, 0.04, 0.02, and 0, we require $\|I_e(t)\|<0.242$, 0.44, 0.615, and 0.797, respectively, for all t. Graphical representations of these error bounds are shown in FIG. 19. We emphasize that these are only bounds that will guarantee a certain value of Λ. As shown herein, even if a stimulus falls outside of a shaded region, the associated Λ may still be larger than the value guaranteed for that shaded region. For a network of neurons without coupling or noise, any stimuli with Λ>0 should be able to desynchronize an initially coupled neural network. However, for real networks, the value of Λ required for desynchronization will depend on the strength of the coupling and noise. A possible variation could be to include taking into account the effect of coupling on the Lyapunov exponent in order to determine the optimal control.

We now compare the energy used by our NCB, event-based control shown in FIGS. 15A-C (which we will refer to as the exponential control) to the energy used by a control that will desynchronize a system of neurons by optimally driving them to a phaseless set (which we will refer to as the phaseless control). For a system obeying Ohm's law, the power P applied by an input is given by P~$u^2$. A representative portion of a comparison over 1500 ms is shown in FIGS. 20A-D. The top two panels show a noisy system of coupled neurons stimulated by the exponential control, while the bottom two panels show the same system stimulated by the phaseless control.

For a single application of the exponential control, $\int_0^{t_1} u^2(t) \approx 2.32$ while for one application of the phaseless control, $\int_0^{t_{end}} u^2(t) \approx 194$. Throughout the simulation, the exponential control is active for more time than the phaseless control; however, one cycle of the exponential control costs much less than one cycle of the phaseless control. Over the entire 1500 ms simulation, we find that the total power used is proportional to 236 and 1904 for the exponential control and the phaseless control, respectively. Not only is the maximum applied control much less for the exponential control, but it also uses nearly an order of magnitude less energy.

Optimally Decreasing Distribution Peak Height for the Reduced Hodgkin-Huxley Model Finally, we look from the perspective of controlling distributions by using the strategy described herein to see if we can find a more effective control to desynchronize (??) than the control that maximizes the Lyapunov exponent. Here, we attempt to provide reasonable values for the still undetermined parameters in the Euler-Lagrange Equations (??)-(??). Because we have undetermined parameters, we cannot claim to have found an optimal stimulus to minimize our cost function, but we can still gather powerful insight about stimuli that will affect network desynchronization. In order to make explicit comparisons to the optimal stimulus which maximizes the Lyapunov exponent, we take $t_1$=10.34 ms. We choose β=8 this time because β=9 gives a solution which is too large in magnitude, and invalidates the phase reduction. As shown herein, we take our initially synchronized distribution to be a normal distribution with standard deviation $\sigma_d$=0.2 centered at θ=0. These conditions were chosen as a reasonable approximation to observed distributions for simulations of the network (??) just before the control threshold $\overline{V}$=−30 mv is reached. This gives $\theta_M(0)$=0 and $\rho_M$=1.995 as initial conditions to (??) and (??). We optimize the cost function over reasonable values of $\lambda_1(0)$, $\lambda_2(0)$ in order to find the best choice for the remaining initial conditions. Using this approach we find $\lambda_1(0)$=6 and $\lambda_2(0)$=0 approximately minimizes the cost function, and gives the stimulus shown in FIG. 21, which will be referred to as $u_D$.

We apply $u_D$ to (??) and (??) with N=250, D=0 and $\alpha_{ij}$=0 to determine the validity of the results found using the phase reduction. For a given neuron, we can deduce its phase at a given time by integrating the reduced Hodgkin-Huxley equations without input or noise until the neuron's next spike. FIGS. 22A-C show three frames in which the mapping $\theta \in (\pi, 2\pi) \rightarrow (-\pi, 0)$ is used, e.g., $$\theta = \frac{3\pi}{2}$$

is plotted as $$\theta = -\frac{\pi}{2}.$$

Theoretical and experimental evolutions are shown in black 2210 and blue 2220, respectively. The red curve 2230 gives the theoretical evolution of the distribution in the absence of stimulus and noise and is shown for reference. Throughout the simulation, the phase reduction well approximates the dynamics of the 250 neuron system, and the optimal stimulus takes $\rho_M$ from 1.995 to approximately 0.7. The stimuli $u_D$ and $u_A$ are nearly identical for the reduced Hodgkin-Huxley mode, with discrepancies in the two answers most likely due to the more restrictive constraints on $u_A$. The similar answers are of interest because we approached the desynchronization problem from two different perspectives.

To gauge whether $u_D$ is an improvement over $u_A$, we simulate (??) same parameters and control strategy as the simulations from FIGS. 18A-D. When we use $u_D$ as the control, the overall energy use is 270 units, while for $I_A$, the energy consumption is 214 units. The cause of this discrepancy is most likely due to the assumption that $u_D$ is Gaussion is no longer valid near the end of the cycle, which wastes a small amount of energy. Results for this simulation do not differ significantly from the results in FIGS. 18A-D (not shown).

Comparison to Pulsatile Input

As mentioned supra, clinical DBS is currently implemented with a high frequency pulsatile input. While the exact mechanism by which this wave form mitigates the symptoms of Parkinson's disease is unknown, it has been postulated that DBS may be effective because it chaotically desynchronizes neurons in the Thalamus region of the brain. They used phase reduction to show that for certain stimulus intensities with frequencies that are approximately twice the natural frequency ($2 \times 1/T$) of a neuron, pulsatile stimuli can effectively desynchronize a population of neurons. We take $\theta \in [0, 1)$ with $\theta=0$ corresponding to the spiking of a neuron and scaled to 1 time unit. We apply our NCB and CB optimization process with $\beta=1.5$ and $t_1=0.85$. The PRC, its first derivative, and the resulting optimal stimuli are shown in FIGS. 23A-C.

The respective Lyapunov exponents for the NCB and CB optimal stimuli from (??) are 1.429 and 1.937, with respective power consumptions ($\int_0^{t_1} u^2 dt$) 1.11 and 1.99. We note that the CB stimulus outperforms the NCB stimulus at the expense of using almost twice as much energy. FIG. 24A-D shows the phase separation of two neurons which obey equation (??) for the PRC shown in FIGS. 23A-C subject to repeated iterations of both the NCB (Panels A and B) and CB (Panels C and D) stimuli. As seen in previous sections, the neurons exponentially desynchronize at a rate determined by their Lyapunov exponents until the neurons are nearly antiphase.

We now apply the NCB optimal stimulus to a population of 100 noisy neurons:

$$\dot{\theta}_i = \omega + Z(\theta_i)[u(t) + A\gamma_i(t) + B\zeta(t)] + \frac{A^2 + B^2}{2} Z(\theta_i) Z'(\theta_i), \quad (29)$$

$$i = 1, \ldots, 100,$$

where $\omega=1$ gives the neural baseline dynamics (recall that $\theta \in [0, 1)$), $\gamma$ and $\zeta$ are individual and common white noise processes with strength $A=\sqrt{0.2}$ and $B=\sqrt{0.3}$ respectively, and $u(t)$ is the common DBS input. The final term in equation (??) corresponds to the Ito term for the phase reduction. In order to determine when the optimal stimulus should be presented, we need to know when the average phase of the system of neurons is $\theta=0$. In real neurons, a spiking event is defined to be $\theta=0$, and can be observed as a sudden increase in voltage. For the model under consideration, we are simulating a phase reduced model, with no observable voltage spikes. In lieu of $V$ for the system of neurons, we monitor the average phase of the system, $$\bar{\theta} = \frac{1}{N} \sum_{i=1}^{N} \theta_i.$$

Note that $\bar{\theta}$ is equivalent to $\psi$ in the first order Kuramoto parameter, $$re^{i\psi} = \frac{1}{N} \sum_{j=1}^{N} e^{i\theta_j}.$$

For a completely synchronized network, $\bar{\theta}$ varies between 0 and 1, while for a network in the splay state, $\bar{\theta}$ remains constant at 0.5. This gives a continuum from which we can qualitatively gauge the level of synchronization by noting the maximum value of $\bar{\theta}$ on a particular cycle. To determine when to apply a new stimulus, a flag is set when $\bar{\theta} > 0.65$, indicating that the network is still sufficiently synchronized, and a new stimulus begins if the flag is set and $\bar{\theta} < 0.5$, indicating that a majority of the neurons have phase $\theta \approx 0$.

To characterize the desynchronization of the neural network, we use the entropy $$\text{Entropy} = \sum_{j=1}^{B} p(\psi_j) \log(p(\psi_j)),$$

where $p(\psi_j)$ is the probability of being in bin j of B total bins. The splay state has the highest entropy for a population of 100 neurons at 4.6.

In previous work the results were computed using a mapping based on the PRC to determine the effect of a DBS pulse. In our trials, we found that adding pulse width somewhat degraded the effectiveness of the pulsatile stimulus. We use equation (??) with $u(t)=0$ for all time, and instead iterate when a pulse stimulus is presented as follows:

$$\theta_{i+1} = \theta_i + Z(\theta_i)\delta,$$

where $\delta$ is the amplitude of the stimulus. For the simulation, we choose $\delta=0.63$ at a frequency of 1.92 Hz. These are in the range with the best desynchronization capabilities for this model. We use an Euler-Maruyama method to solve (??) for both the optimal and pulsatile stimulus, with results shown in FIGS. 25A-D. We find that both stimuli are able to desynchronize the population to similar levels as characterized by the entropy of the system. However, the pulsatile input takes approximately 15 seconds and 29 pulses for the entropy to reach a reasonably steady entropy value of 3.5, while it only takes 5 seconds and three applications of the optimal stimulus to increase the entropy to 3.5. Assuming the power usage $P \sim u^2$, we cannot directly approximate the energy required by the pulsatile input since it has no pulse-width (PW). However, in human trials, pulsatile inputs have been used with a PW to period ratio of $7.8 \times 10^{-3}$ and $9.5 \times 10^{-3}$ respectively. We take the average of these two ratios to estimate a pulse-width and require $PW \cdot u = \delta$, and find that $PW \sim 0.0045$ and $u \sim 155$ in order to be therapeutically effective. Letting the power consumption, $P = u^2 \cdot PW$, we find that $P \sim 108$ units. Conversely, for the optimal stimulus, $\int_0^{t_1} u^2 dt \sim 1.11$. As a very rough estimate of total energy used to achieve steady desynchronization, three applications of the optimal stimulus use 3.33 units of energy while 29 applications of the pulsatile stimulus use 3132 units of energy. Both stimuli are able to desynchronize the neural network, but the optimal stimulus is able to do so using three orders of magnitude less energy.

Embodiments of the present invention can be envisioned as methods, devices and/or systems incorporating one or more brain stimulator devices, stimulating and recording electrodes, one or more computer programs executable by a computer device or a programmable chip and/or one or more signal measuring devices. Embodiments can also be envisioned as including implantable devices or microprocessors.

CONCLUSION

We have described two methods for desynchronizing neural networks: by optimally maximizing the Lyapunov exponent (??) and optimally decreasing the peak height of the phase distribution. Most notably, while both of these methods are based on different perspectives, they produce answers that are quite similar. We find that this method uses three orders of magnitude less energy than a method that uses pulsatile stimuli to achieve desynchronization, which represents an enormous potential savings in battery life of a pacemaker and could also mitigate some of the negative side-effects of DBS. We have also shown that the approach for maximizing the Lyapunov exponent is robust to inaccuracies in finding the optimal stimulus and found bounds for a stimulus derived from a network without coupling that will guarantee a minimum Lyapunov exponent required to give desynchronization for a given network with coupling. Because this method is robust to inaccuracies, it has potential to work well in an in vitro setting, and could realistically provide an effective treatment for Parkinson's disease.

The invention claimed is:

1. A method of brain stimulation for treatment of a neurological disease, comprising:
   (a) stimulating neurons in a brain region;
   (b) measuring or calculating a phase response curve for a population of interest of said stimulated neurons; and
   (c) calculating by a computer programmed device and using said measured or calculated phase response curve, stimulus parameters and waveforms to synchronize or desynchronize neuronal oscillators in said brain region, wherein said calculation is based on a Lyapunov exponent described in terms of said measured or calculated phase response curve.

2. The method as set forth in claim 1, wherein said neurons are neurons from the basal ganglia.

3. The method as set forth in claim 1, wherein said neurological disease is Parkinsons disease.

4. The method as set forth in claim 1, wherein said calculation produces a stimulus which considers a trade-off between a reduction in peak height of a phase density and an expenditure of energy.

5. The method as set forth in claim 1, wherein said calculation produces a stimulus designed to increase the entropy of a population of neurons.

\* \* \* \* \*